US010903019B2

(12) United States Patent
Mallick et al.

(10) Patent No.: US 10,903,019 B2
(45) Date of Patent: Jan. 26, 2021

(54) COMPOSITIONS AND METHODS OF MAKING METAL-ORGANIC FRAMEWORKS WITH REDOX-ACTIVE CENTERS

(71) Applicant: King Abdullah University of Science and Technology, Thuwal (SA)

(72) Inventors: Arijit Mallick, Thuwal (SA); Bilal Ahmed, Thuwal (SA); Osama Shekhah, Thuwal (SA); Husam N. Alshareef, Thuwal (SA); Mohamed Eddaoudi, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 16/471,812

(22) PCT Filed: Dec. 29, 2017

(86) PCT No.: PCT/IB2017/058522
§ 371 (c)(1),
(2) Date: Jun. 20, 2019

(87) PCT Pub. No.: WO2018/122797
PCT Pub. Date: Jul. 5, 2018

(65) Prior Publication Data
US 2020/0118768 A1   Apr. 16, 2020

Related U.S. Application Data

(60) Provisional application No. 62/440,573, filed on Dec. 30, 2016.

(51) Int. Cl.
*H01G 11/30* (2013.01)
*C07D 471/06* (2006.01)
*C07F 7/00* (2006.01)
*H01G 11/86* (2013.01)

(52) U.S. Cl.
CPC ........... *H01G 11/30* (2013.01); *C07D 471/06* (2013.01); *C07F 7/003* (2013.01); *H01G 11/86* (2013.01)

(58) Field of Classification Search
CPC .............................. C07D 471/06; C07F 7/003
See application file for complete search history.

(56) References Cited

U.S. PATENT DOCUMENTS

2012/0077092 A1   3/2012   Lee et al.
2016/0336619 A1   11/2016  Choi et al.

FOREIGN PATENT DOCUMENTS

EP   2291384 A2   3/2011

OTHER PUBLICATIONS

Klein. Journal of the American Chemical Society, 2015, 137, 11011-11021 (Year: 2015).*
Notification of Transmittal of the International Search Report and the Written Opinion of the International Searching Authority, or the Declaration for PCT/IB2017/058522 dated Mar. 21, 2018.
Zhang, et al., "Redox-active metal-organic frameworks as electrode materials for batteries", MRS Bulletin, vol. 11, http:/www.cambridge.org/core/terms. http://dx.doi.org/10.1557/mrs.2016.245, Nov. 2016, 883-889.
Campagnol, et al., "A Hybrid Supercapacitor Based on Porous Carbon and the Metal-Organic Framework MIL-100 (Fe)", Chemelectrochem, vol. 1, Jun. 2014, pp. 1-8.
Chen, et al., "Recent Advancements in Electrode Materials for the Highperformance Electrochemical Supercapacitors: A Review", International Journal of Electrochemical Science, vol. 9, May 19, 2014, pp. 4072-4085.
Choi, et al., "Supercapacitors of Nanocrystalline Metal-Organic Frameworks", ACS Nano, vol. 8, No. 7, Jul. 7, 2014, pp. 7451-7457.
Deblase, et al., "Cation-Dependent Stabilization of Electrogenerated Naphthalene Diimide Dianions in Porous Polymer Thin Films and Their Application to Electrical Energy Storage", Angewandte Chemie International Edition, vol. 54, Sep. 2015, pp. 1-6.
Deblase, et al., "β-Ketoenamine-Linked Covalent Organic Frameworks Capable of Pseudocapacitive Energy Storage", Journal American Chemical Society, vol. 135, Oct. 22, 2013, pp. 16821-16824.
Ogihara, et al., "A Self-Assembled Intercalated Metal-Organic Framework Electrode With Outstanding Area Capacity for High Volumetric Energy Asymmetric Capacitors", Journal of Materials Chemistry A, vol. 4, Jan. 2016, pp. 3398-3405.

(Continued)

*Primary Examiner* — Noble E Jarrell
(74) *Attorney, Agent, or Firm* — Billion & Armitage; Gregory S. Schwartz

(57) ABSTRACT

Embodiments of the present disclosure describe an electrode material comprising a metal ion cluster and an organic linker with a redox-active center associated with the metal ion cluster sufficient to form a metal-organic framework. Embodiments of the present disclosure further describe a method of forming an electrode material comprising contacting a metal ion cluster with an organic linker including a redox-active center sufficient to form a metal-organic framework. Embodiments of the present disclosure also describe a metal-organic framework composition comprising a metal ion cluster and an organic linker with a redox-active center associated with the metal ion cluster.

13 Claims, 23 Drawing Sheets

(56) References Cited

OTHER PUBLICATIONS

Rakhi, et al., "Substrate Dependent Self-Organization of Mesoporous Cobalt Oxide Nanowires with Remarkable Pseudocapacitance", Nano Letters, vol. 12, Apr. 11, 2012, pp. 2559-2567.

Salunkhe, et al., "Fabrication of Symmetric Supercapacitors Based on MOF-derived Nanoporous Carbons", Journal of Materials Chemistry A, vol. 2, Oct. 2014, pp. 19848-19854.

Sheberla, et al., "Conductive MOF Electrodes for Stable Supercapacitors With High Areal Capacitance", Nature Materials, vol. 16, Oct. 2016, pp. 220-224.

Song, et al., "Polyimides: Promising Energy-Storage Materials", Angewandte Chemie International Edition, vol. 49, 2010, pp. 8444-8448.

Wang, et al., "Flexible Solid-State Supercapacitor Based on a Metal-Organic Framework Interwoven by Electrochemically-Deposited PANI", Journal of the American Chemical Society, vol. 137, 2015, 4 pages.

Wu, et al., "Graphene/Metal Oxide Composite Electrode Materials for Energy Storage", Nano Energy, vol. 1, Jan. 2012, pp. 107-131.

Yang, et al., "Zn-Doped Ni-MOF Material with a High Supercapacitive Performance", Journal of Materials Chemistry A, Sep. 2014, 6 pages.

Zhi, et al., "Nanostructured Carbon-Metal Oxide Composite Electrodes for Supercapacitors: A Review", Nanoscale, vol. 5, 2013, pp. 72-88.

\* cited by examiner

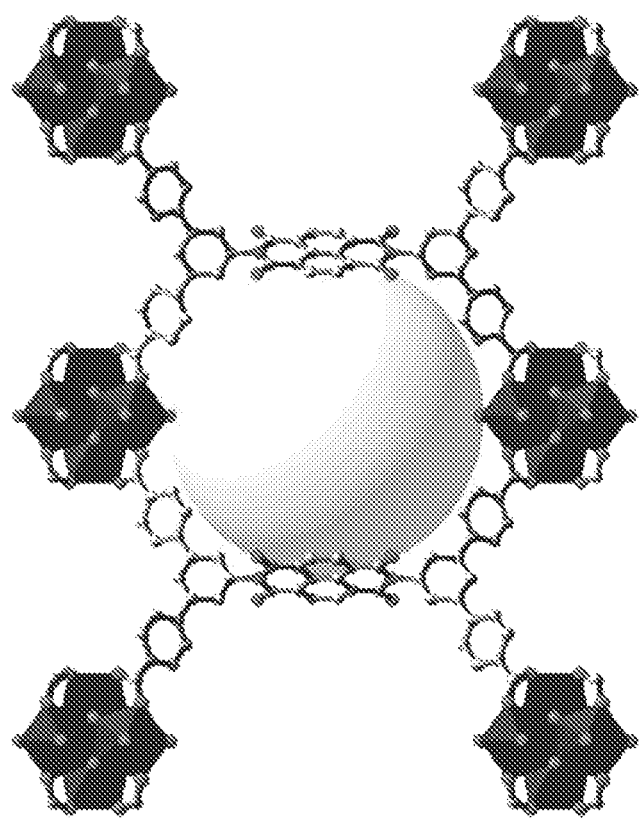
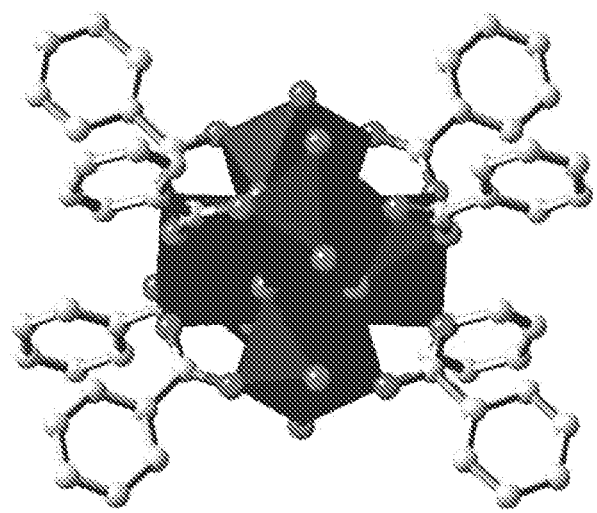
FIG. 8A
FIG. 8B

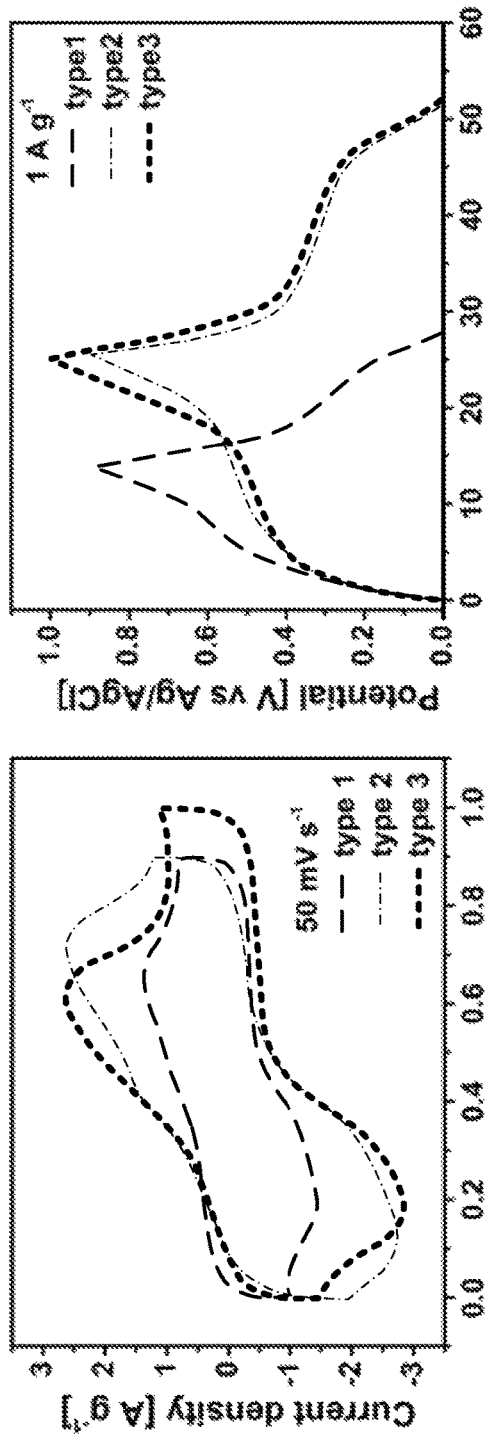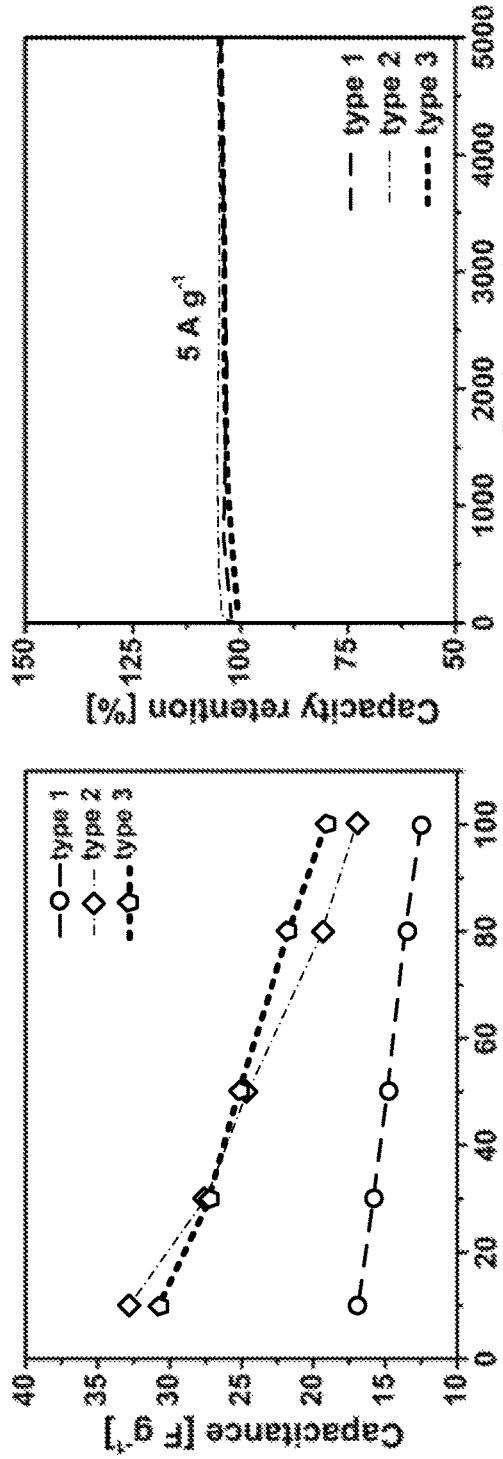
FIG. 13A  FIG. 13B  FIG. 13C  FIG. 13D

COMPOSITIONS AND METHODS OF MAKING METAL-ORGANIC FRAMEWORKS WITH REDOX-ACTIVE CENTERS

BACKGROUND

Energy storage nowadays is considered a key element in most renewable energy systems. Existing technologies, such as wind turbines and solar photovoltaics are intermittent by nature. Thus, energy storage technologies (e.g., batteries and supercapacitors (SC)) have the potential to mitigate this intermittency problem of renewable energy sources, through storing the generated energy for later use upon demand. Supercapacitors are becoming important storage technology due to their charge storage mechanism, which does not involve irreversible chemical reactions. Stable porous materials are considered attractive electrode materials for capacitive energy storage applications, since they provide high surface areas, and their open structures can enhance rapid ion transport. These features can increase capacitance and rate performance of the supercapacitors.

Supercapacitors exemplify an importance class of energy storage devices largely due to their high power density. Supercapacitors are useful for heavy electrical vehicles that need to burst electrical power for rapid acceleration (e.g., electric vehicles, high-speed bullet trains, elevators in high-rise buildings, weight-lifting cranes, hill-climbing cars, etc.). Generally, battery power has been utilized to accelerate vehicles, for example, but supercapacitors provide an efficient release of power that is much quicker than batteries. In addition, as compared to batteries, supercapacitors require no maintenance, offer high cycle-life, require only a simple charging circuit, experience no "memory effect," and operate under safer conditions. Commercial supercapacitors use porous carbon and graphene, electrodes which operate at a very high charge/discharge rate, and have a long cycle life. However, emerging applications demand even higher capacitances. In contrast, pseudocapacitive materials with redox-active metal centers have higher capacitance, but shorter cycle life.

As a result, there is a need to develop electrodes that combine both redox and electric double layer capacitances with long cycle life.

SUMMARY

In general, embodiments of the present disclosure describe a metal-organic framework composition, electrode materials, and methods of forming a metal-organic framework and electrode material.

Accordingly, embodiments of the present disclosure describe an electrode material comprising a metal ion cluster and an organic linker with a redox-active center associated with the metal ion cluster sufficient to form a metal-organic framework.

Embodiments of the present disclosure further describe a method of forming an electrode material comprising contacting a metal ion cluster with an organic linker including a redox-active center sufficient to form a metal-organic framework.

Another embodiment of the present disclosure is a metal-organic framework composition comprising a metal ion cluster and an organic linker with a redox-active center associated with the metal ion cluster.

The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which:

FIGS. 8A-8B are schematic diagrams illustrating (a) the crystal structure of Zr-BTD-NDI-MOF along the a-axis, and (b) the hexanuclear Zr-cluster with 8 carboxylate form the linker, according to one or more embodiments of the present disclosure.

FIGS. 13A-13D relate to MOF electrodes for supercapacitors in 1 M $H_2SO_4$ and illustrate (a) graphical views of CV curves collected at 50 mV s$^{-1}$, (b) graphical views of GCD profiles at 1 A g$^{-1}$, (c) graphical views of capacitance as a function of scan rate (mV s$^{-1}$), and (d) graphical views of stability tests performed at 5 A g$^{-1}$, according to one or more embodiments of the present disclosure.

DETAILED DESCRIPTION

Figure 1:
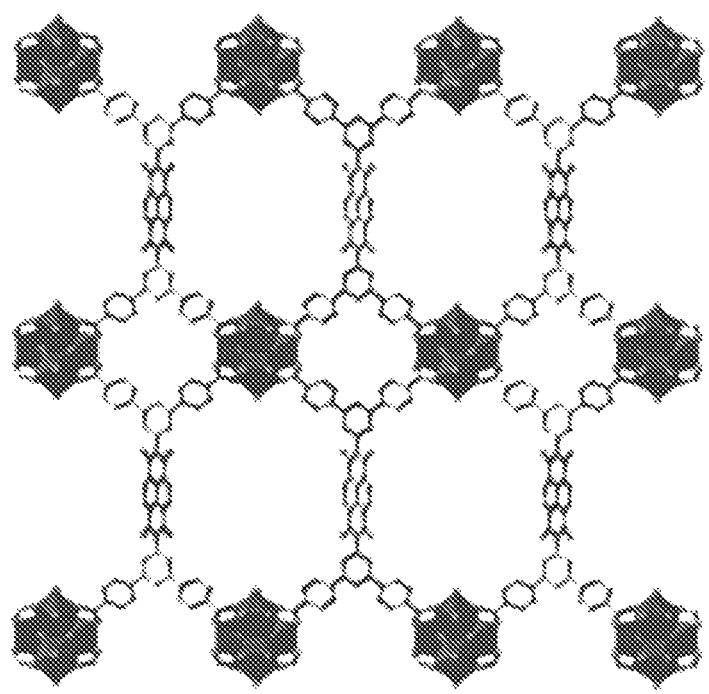
FIG. 1 is a schematic diagram of a metal-organic framework with a redox-active center, according to one or more embodiments of the present disclosure.

The invention of the present disclosure relates to electrode materials. In particular, the invention of the present disclosure relates to electrode materials including organic linkers with redox-active centers that associate with metal ion clusters sufficient to form a metal-organic framework (MOF). This is the first time a stable and rigid metal-organic framework has been fabricated with a redox-active center for enhancing faradaic energy storage. The redox-active centers of the organic linkers permit the storage of electrical energy via pseudocapacitance (e.g., metal-oxide and/or electrochemical pseudocapacitance), as well as modification and tuning of the performance characteristics of the electrode material. The high surface area and uniform pore distribution of the metal-organic frameworks enhances the storage of electrical energy via double-layer capacitance (e.g., electrostatic double-layer capacitance). In this way, the electrode materials exhibit the high performance characteristics necessary for a variety of applications, including electrochemical capacitors (e.g., supercapacitors).

The electrode materials of the present disclosure include metal-organic frameworks. Metal-organic frameworks are modular crystalline porous materials composed of both organic (e.g., organic linkers and/or ligands) and inorganic components (e.g., metal ions and/or metal ion clusters) arranged in a periodic networked structure. A feature of metal-organic frameworks of the present disclosure is that the organic and inorganic components may be tuned to target and design metal-organic frameworks with high capacitance and long life cycle behavior. The metal-organic frameworks of the present disclosure have been tuned to integrate different functionalities (e.g., redox centers) in their structure by using strategically designed organic linkers that have the targeted center for supercapacitor applications. Metal-organic frameworks also exhibit one or more of high and/or uniform porosity, high surface area, and chemical stability. In many embodiments, the metal-organic framework is utilized as an electrode material for supercapacitors. In other embodiments, the metal-organic framework may be utilized as an electrode separator and/or in lithium-ion batteries. These embodiments, however, are not limiting and the metal-organic framework of the present disclosure may be utilized in any application known to a person of skill in the art.

The metal-organic frameworks of the present disclosure may be integrated in supercapacitors (e.g., as electrode materials). Supercapacitors generally require high performing electrode materials and outperform other types of capacitors, including electrolytic capacitors and batteries, with respect to energy density (e.g., amount of energy stored per unit volume or more), rate performance (e.g., rate of accepting and delivering charge), and life cycle (e.g., number of charge and discharge cycles before failure). While most capacitors include a solid dielectric between two electrodes, supercapacitors do not utilize a solid dielectric. Rather, supercapacitors include an electrolyte and a separator (e.g., ion-permeable membrane) between two electrodes. When a voltage is applied, a monolayer of solvent molecules at the electrode-electrolyte interface forms that functions as a thin molecular dielectric.

FIG. 1 is a schematic diagram of a metal-organic framework with a redox-active center, according to one or more embodiments of the present disclosure. Metal-organic frameworks, such as the one shown in FIG. 1, may be utilized as electrode materials in supercapacitors, for example. Embodiments of the present disclosure describe an electrode material that includes a metal ion cluster and an organic linker with a redox-active center that associates with the metal ion cluster sufficient to form a metal-organic framework.

The metal ion cluster may include a polynuclear inorganic building block. In some embodiments, the metal ion cluster may be characterized by the formula $[M_6O_4(OH)_4]^{12+}$, where M includes one or more of an alkali metal, rare-earth metal, transition metal, lanthanide, and/or post-transition metal. Alkali metals may include one or more of lithium, sodium, potassium, rubidium, caesium, and francium. Rare-earth metals may include one or more of cerium, dysprosium, erbium, europium, gadolinium, holmium, lanthanum, lutetium, neodymium, praseodymium, promethium, samarium, scandium, terbium, thulium, ytterbium, and yttrium. Transition metals may include one or more of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, darmstadtium, roentgenium, and copernicium. Lanthanides may include one or more of lanthanum, cerium, praseodymium, neodymium, promethium, samarium, europium, gadolinium, terbium, dysprosium, holmium, erbium, thulium, ytterbium, and lutetium. Post-transitiona metals may include one or more of aluminum, gallium indium, tin, thallium, lead, bismuth, nihonium, flerovium, moscovium, and livermorium.

The organic linker may include a ligand with a redox-active center. In many embodiments, the organic linker is N,N'-bis(terphenyl-4,4"-dicarboxylic acid) naphthalene-diimide, wherein N,N'-bis(terphenyl-4,4"-dicarboxylic acid) is the ligand and naphthalenediimide (NDI) is the redox-active core. In other embodiments, the organic linker may include one or more of anthraquinone, benzoquinone, perylinedianhydride, and organic nitroxide radicals.

The metal ion cluster and organic linker with a redox-active center associate to form a metal-organic framework. The metal-organic framework may include a scu topology. The metal-organic frameworks may exhibit high stability towards moisture, low pH media, and electrolyte medium (e.g., including acidic conditions), leading to a long cycle life relative to conventional materials. In some embodiments, the metal ion clusters provide high chemical stability and increase the life cycle of the capacitor. The redox-active centers of the organic linkers permit the storage of electrical energy via pseudocapacitance (e.g., metal-oxide and/or electrochemical pseudocapacitance), as well as modification and tuning of the performance characteristics of the electrode material (e.g., associated redox capabilities). The open and/or periodic structure, high surface area, and uniform pore distribution of the metal-organic frameworks increase the storage of energy via double-layer capacitance (e.g., electrostatic double-layer capacitance) and facilitate rapid ion transport without blocking the accessible pore system/surface area. The resulting metal-organic framework is an electrode material with high capacitive performance.

The metal-organic framework may exhibit a high porosity, a high surface area, and/or uniform pore distribution. In many embodiments, the surface area of the metal-organic framework is equal to or greater than about 1,000 $cm^2/g$. Whereas conventional carbon-based electrodes (e.g., activated carbon electrodes) suffer from low capacitance (e.g., about 10% capacitance) due to irregular porosity distribution, the metal-organic frameworks exhibit a uniform or nearly uniform pore distribution. Conventional electrodes also suffer from inaccessible micropores due to electrolyte blocking, resulting in a formation of double layers on the surface only (about 2 nm depth), as opposed to the entire pore system. Metal-organic frameworks, on the other hand, are highly porous and exhibit uniformly accessible porosity.

The electrode material may store electrical energy via one or more of double-layer capacitance and pseudocapacitance. In many embodiments, the electrode material stores electrical energy via double-layer capacitance and pseudocapacitance. The storage of electrical energy via double-layer capacitance may be based on electrostatic forces and not on charge transfer between electrode and electrolyte. In particular, double-layer capacitance may include the formation of a monolayer of solvent molecules at the electrode-electrolyte interface between two electrical layers. One of the layers may be formed in a lattice structure of the electrode (e.g., metal-organic framework) and the other layer of solvated ions with opposite polarity may form in the electrolyte. The monolayer of solvent molecules may adsorb to the surface of the electrode and functions as a thin molecular dielectric by separating charge at the interface between the electrode and the electrolyte. Pseudocapacitance, on the other hand, is the storage of electrical energy via faradaic redox reactions, intercalation, and/or adsorption. In an electrochemical capacitor, an electron charge-transfer occurs when a de-solvated ion comes out of the electrolyte, pervades the double-layer, and adsorbs on a surface of the electrode. In many embodiments, the electrode material exhibits a high areal supercapacitor performance that may be about a 15-fold increase over conventional materials (e.g., activated carbon). In embodiments where the materials are post-functionalized with an organic pillar, the areal supercapacitor performance may be about a 19-fold increase over conventional materials.

The electrode material may further include an organic pillar. For example, the electrode material may be further tuned via post-functionalization with an organic pillar. The organic pillar may further increase a rigidity and surface area of the electrode material and/or metal-organic framework. The electrode material may be tuned with an organic pillar without affecting redox activity (e.g., maintaining the same redox activity) of the redox-active center of the organic linker. In many embodiments, the organic pillar includes biphenyl-dicarboxylic acid. In other embodiments, the organic pillar includes one or more of pillar linkers, such as one or more of 2,2-bipyridine-4,4-dicarboxylic acid, and 3,3-dihydroxybipheyl-4,4-dicarboxylic acid.

Figure 2:
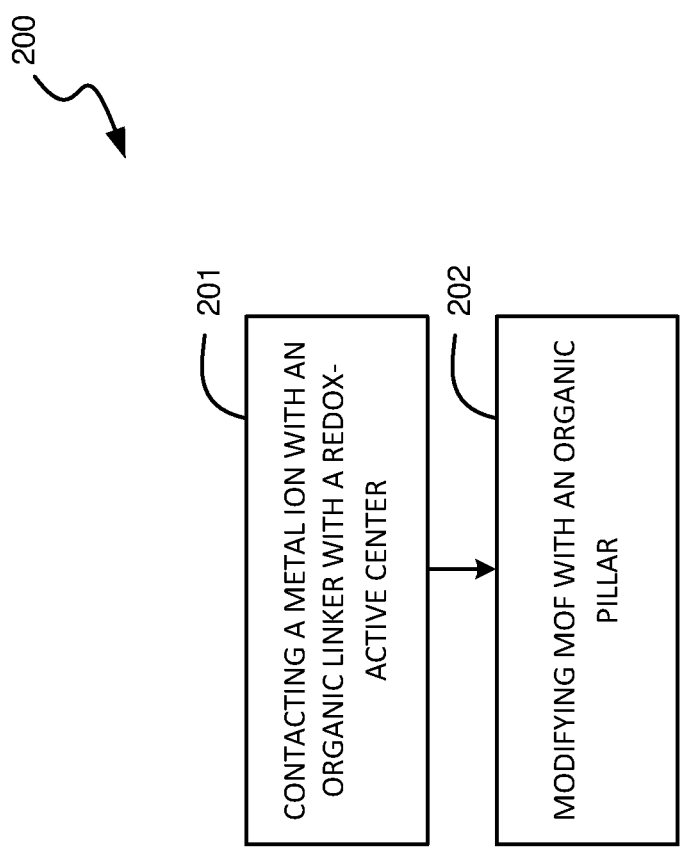
FIG. 2 is a flowchart of a method of forming an electrode material, according to one or more embodiments of the present disclosure.

FIG. 2 is a flowchart of a method of forming an electrode material, according to one or more embodiments of the present disclosure. Any of the embodiments described in the present disclosure may be utilized with respect to this embodiment.

At step 201, a metal ion may be contacted with an organic linker including a redox-active center. Any of the metal ions/metal ion clusters, organic linkers, and/or redox-active centers discussed above may be utilized with respect to step 201. In many embodiments, a metal ion cluster may be contacted with an organic linker including a redox-active center sufficient to form a metal-organic framework. As used herein, "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo. Accordingly, treating, tumbling, vibrating, shaking, mixing, and applying are forms of contacting to bring two or more components together.

At step 202, the metal-organic framework may be modified with an organic pillar. Any of the organic pillars discussed above may be utilized with respect to step 202. In many embodiments, the metal-organic framework is modified via post-functionalization with an organic pillar. As used herein, "modifying" refers to adjusting, introducing, installing, contacting, providing, altering, adding, treating, and any other similar terms understood by a person of skill in the art. Post-functionalization generally refers to chemical treatment of a fabricated metal-organic framework, with the structure remaining intact. By modifying the metal-organic framework in this way, the surface area and rigidity of the metal-organic framework may be tuned (e.g., increased and/or enhanced). Step 202 is optional.

Alternatively, in other embodiments, metal-organic frameworks may be fabricated by utilizing pristine metal-organic frameworks to store electrical energy on internal surfaces through electrochemical double-layer capacitance or redox reactions of a metal center may be exploited to store energy. In other embodiments, metal-organic frameworks may be fabricated by decomposing/destroying metal-organic frameworks to afford metal or metal-oxides and to store energy faradaically via charge transfer between electrolyte and electrolyte. In other embodiments, metal-organic frameworks may be fabricated by pyrolyzing metal-organic frameworks to give microporous carbons and enhance capacitance by increasing conductivity. These methods may be used alone or in any combination to fabricate metal-organic frameworks.

The following Examples are intended to illustrate the above invention and should not be construed as to narrow its scope. One skilled in the art will readily recognize that the Examiners suggest many other ways in which the invention could be practiced. It should be understand that numerous variations and modifications may be made while remaining within the scope of the invention.

Example 1

Zr-NDI-MOF and Zr-NDI-BPD-MOF

Supercapacitors are attractive power sources, compared with batteries. Supercapacitors require no maintenance, offer a high cycle-life, require only a simple charging circuit, experience no "memory effect," and are generally much safer. Physical energy storage—as opposed to chemical energy storage—is a key reason for their safe operation and extraordinarily high cycle-life. Supercapacitors' high energy density has fueled a growing interest in supercapacitors in the electronics industry. Stable and porous materials are attractive for capacitive energy storage because they provide high surface areas for increased double-layer capacitance, open structures for rapid ion transport, and redox-active centers that enable faradaic (pseudocapacitive) energy storage. Porous carbon and graphene are commercially used supercapacitors, which operate at a very high charge/discharge rate with a long life cycle. However, carbon- and graphene-based supercapacitors have low capacitance. In contrast, metal-oxide pseudocapacitors exhibit high capacitance, but redox reactions lead to low life cycle.

The following Example describes, for the first time, the synthesis of a pre-designed Zr-based-MOF having a redox active organic linker and the use of it as a supercapacitor electrode. A naphthalenediimide (NDI) core has deliberately been incorporated as the redox center in the organic linker, which exhibited a two-step redox process. The combination of the high porosity of the designed Zr-NDI-MOF with the redox centers, contributed double-layer and pseudo-capacitance, respectively, led to enhancing the capacitance performance of this new MOF. The possibility also to post-synthetically modify the Zr-NDI-MOFs using organic pillars led to an enhancement in the surface area and increased the capacitance performance of this MOF by a factor of at least two.

Materials and Methods

All reagents were obtained from commercial sources and used without further purification, unless otherwise noted. Powder X-ray diffraction (PXRD) measurements were carried out at room temperature on a PANalyticalX'Pert PRO diffractometer 45 kV, 40 mA for Cu Kα ($\lambda$=1.5418 Å), with a scan speed of $1.0°$ min$^{-1}$ and a step size of $0.02°$ in 2θ. Variable Temperature Powder X-ray Diffraction (VT-PXRD) measurements were collected on a PANalyticalX'Pert Pro MPD X-ray diffractometer equipped with an Anton-Parr CHC+ variable temperature stage. Measurements were collected at 45 kV, 40 mA for Cu Kα ($\lambda$=1.5418 Å) with a scan speed of $1.0°$ min$^{-1}$ and a step size of $0.02°$ in 2θ. Samples were placed under vacuum during analysis and the sample was held at the designated temperatures for at least 15 minutes between each scan. High resolution dynamic thermogravimetric analysis (TGA) were performed under a continuous $N_2$ flow and recorded on a TA Instruments hi-res TGA Q500 thermogravimetric analyzer with a heating rate of $1°$ C. per minute. Fourier-transform Infrared (FT-IR) spectra (4000-600 cm$^{-1}$) were recorded on a Thermo Scientific Nicolet 6700 apparatus. Low pressure gas adsorption studies of the MOFs were conducted on a fully automated micropore gas analyzer Autosorb-IC (Quantachrome Instruments) at relative pressures up to 1 atm. The temperature was controlled using a cryocooler system (cryogen-free) capable of temperature control from 20 to 320 K.

Synthesis of Ligands and Metal Organic Frameworks (MOFs).

Scheme 1 is a reaction scheme for the synthesis of ligands from starting materials:

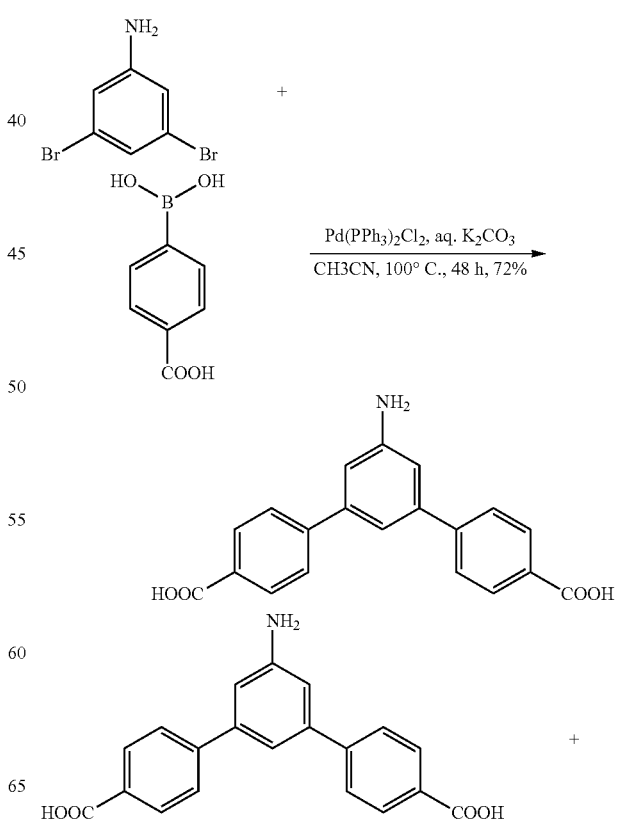

-continued

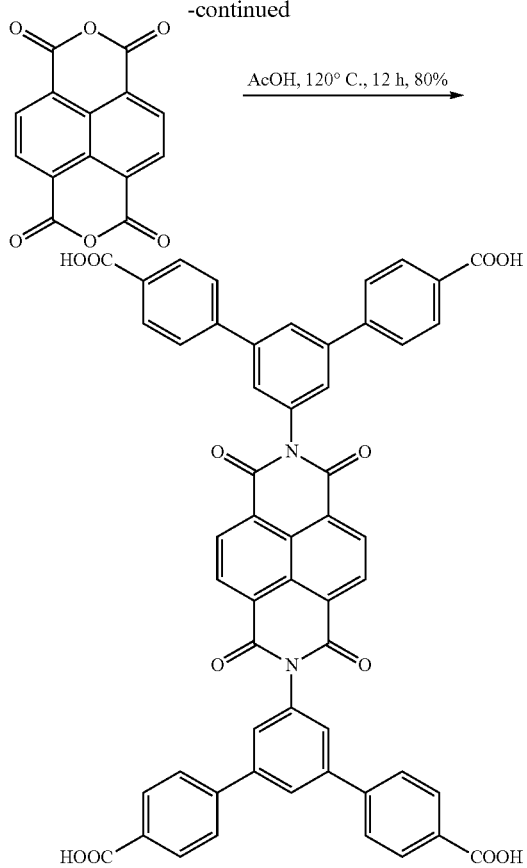

Preparation of anilene-3,5-dibenzoicacid

CH$_3$CN (40 ml) was placed in a 250 ml round-bottom flask sealed with septum, the flask was evacuated/backfilled with argon 3×, then solvent was bubbled with argon for 1.5 h. 1,3-Dibromo-anilene (1.83 g; 10 mmol), 4-carboxyphenylboronic acid (3.66 g; 22 mmol), 5% Pd(PPh$_3$)$_2$Cl$_2$ (0.4 g) and 40 mL aqueous potassium carbonate (5.3 g; 80 mmol) solution were then added, the flask was evacuated/backfilled with argon 3× and heated at 100° C. for 48 h with vigorous stirring. It was cooled to room temperature and the mixture was diluted with water (200 ml), filtered through paper, filter cake was washed thoroughly with water, the filtrate acidified to pH=1 with 2 N HCl and the precipitate was filtered, washed with water, followed by hexane, dried briefly on air, then at high vacuum at 50° C. overnight to give 3.11 g (79%) of white powder in sufficient purity. The NMR data match the reported values.

Preparation of N,N'-bis(terphenyl-4,4''-dicarboxylic Acid) naphthalenediimide (H4BTD-NDI)

1,4,5,8-tetracarboxydianhydride (0.268 g, 1.0 mmol) was taken into a 250 mL round bottomed flask and suspended in 25 mL acetic acid. The mixture was stirred for 10 min. To this solution, anilene-3,5-dibenzoicacid (0.698 g, 2.2 mmol) was added and the solution allowed reflux for 12 h. The reaction was allowed to cool to room temperature and water (90 ml) was added to precipitate the product. The product was collected by filtration, washed with ethanol, and dried in vacuum to yield 2.4 g of off-white solid (isolated yield=2.4 g, 77%). The compound was recrystallized from DMF as an off-yellow materials (isolated yield=2.1 g, 67%).

Synthesis of the Zr-BTD-NDI-MOF 15 mg ZrCl$_4$ (0.064 mmol) was taken into a 20 mL glass scintillation vial containing NDI-linker (6.0 mg, 0.006 mmol) and 3 mL DMF. To this 400 mg F-BzA and 0.3 mL formic acid were added. This reaction mixture was sonicated for 5 min, placed into a preheated oven at 120° C. for 48 hours, and cooled to room temperature yielding light yellow needle shaped crystals. Single crystals of the MOFs were collected and washed with DMF. The crystals were stored in the same solvent for further application and characterizations.

Synthesis of the Zr-BTD-NDI-BP-MOF & Zr-BTD-NDI-BPy-MOF

Compounds 2 and 3 were synthesized by the linker installation of Zr-BTD-NDI-MOF with BP (4,4'-biphenyl-dicarboxylate) and BPy (2,2'-bipyridine-4,4'-dicarboxylate), respectively, through an acid and base reaction. Scheme 1 shows the chemical equation of linker installation process. Generally, Zr-BTD-NDI-MOF (100 mg) were treated with the solution of linear linkers in DMF (0.03 M, 40 mL) at 85° C. for 24 h. The materials were collected by filtration and washed with fresh DMF 3 times (yield: 96%).

Single Crystal XRD and Crystal Structure of Zr-BTD-NDI-MOF.

SCXRD data of 1 were collected using Bruker X8 PROSPECTOR APEX2 CCD diffractometer using Cu Kα (λ=1.54178 Å) radiation. Indexing was performed using APEX2 (Difference Vectors method). Data integration and reduction were performed using SaintPlus 8.34A. Absorption correction was performed by multi-scan method implemented in SADABS. Space group was determined using XPREP implemented in APEX2. Structure was solved using Direct Methods (SHELXS-2013) and refined using SHELXL-2014 (full-matrix least-squares on F2) contained WinGX. Crystal data and refinement conditions are shown in Table 51. A full list of restraints and constraints is contained within the CIF file. A set of DFIX, SADI, FLAT and RIGU was applied on organic ligand to make its geometry and thermal parameters reasonable. All attempts to refine peaks of residual electron density as solvent molecules were unsuccessful. The data were corrected for delocalized electron density using of the SQUEEZE procedure as implemented in PLATON. The total solvent-accessible void volume of 13337 Å with a total electron count of 5406 was found in the unit cell.

TABLE 1

Crystal data and structure refinement conditions for Zr-BTD-NDI-MOF

| | |
|---|---|
| Empirical formula | $C_{108}H_{68}N_4O_{40}Zr_6$ |
| Formula weight | 2608.98 |
| Crystal system, space group | Orthorhombic, Cmmm |
| Unit cell dimensions | a = 20.7974 (9) Å, |
| | b = 34.320 (1) Å, |
| | c = 24.2844 (9) Å |
| Volume | 17333(1) Å$^3$ |
| Z, calculated density | 2, 0.500 Mg m$^{-3}$ |
| F(000) | 2608 |
| Temperature (K) | 100.0(1) |
| Radiation type, □ | Cu K□□□1.54178 Å |
| Absorption coefficient | 1.67 mm$^{-1}$ |

TABLE 1-continued

Crystal data and structure refinement conditions for Zr-BTD-NDI-MOF

| | |
|---|---|
| Absorption correction | Multi-scan |
| Max and min transmission | 0.125 and 0.041 |
| Crystal size | 0.003 × 0.03 × 0.15 mm |
| Shape, colour | Plate, colourless |
| θ range for data collection | 4.4-50.4° |
| Limiting indices | −20 ≤ h ≤ 20, −34 ≤ k ≤ 21, −23 ≤ l ≤ 24 |
| Reflection collected/unique/observed with I > 2 s(I) | 22259/4918 ($R_{int}$ = 0.053)/3701 |
| Completeness to $\theta_{max}$ = 50.4° | 99.4% |
| Refinement method | Full-matrix least-squares on $F^2$ |
| Data/restraints/parameters | 4918/192/216 |
| Final R indices [I > 2s(I)] | $R_1$ = 0.052, $wR_2$ = 0.172 |
| Final R indices (all data) | $R_1$ = 0.062, $wR_2$ = 0.177 |
| Weighting scheme | $[s^2(F_o^2) + (0.1207P)^2]^{-1}$* |
| Goodness-of-fit | 1.06 |
| Largest diff. peak and hole | 0.49 and −0.59 e Å$^{-3}$ |

*$P = (F_o^2 + 2F_c^2)/3$

High-resolution dynamic thermal gravimetric analysis (TGA) was performed under a continuous $N_2$ flow (25 mL/min) with a heating rate of 1° C./min using a hi-res TGA Q500 thermal gravimetric analyzer. Low-pressure gas sorption measurements were performed on a fully automated micropore gas analyzer Autosorb-IC (Quantachrome Instruments) at relative pressures up to 1 atm. The powder X-ray diffraction patterns and the variable-temperature and variable-humidity powder X-ray diffraction patterns (VT-PXRD and VH-PXRD) were collected over the 2θ range 4-40° on a high-resolution PANalytical X' Pert MPDPRO X-ray diffractometer with Cu Kα1 radiation (λ=1.5406 Å, 45 kV/40 mA) equipped with an Anton-Parr CHC+ variable-temperature stage, with a scan speed of 1°/min and a step size of 0.03° in 2θ. The sample was placed under vacuum during analysis and held at the designated temperatures for at least 20 min between each scan. Single-crystal X-ray diffraction data were collected using (1) an X8 Prospector APEX2 CCD diffractometer (Cu Kαλ=1.54178 Å) and (2) a Bruker Apex 2 DUO CCD diffractometer with a multilayer monochromator (Mo Kαλ=0.71073 Å).

Electrochemical Measurements.

The electrochemical measurements were performed on a Bio-Logic VMP3 potentiostat in both 3-electrode and 2-electrode configurations using 1 M $H_2SO_4$ as electrolyte at room temperature. In 3-electrode measurements, the MOF material was mixed with carbon black and polyvinylidene fluoride (PVDF) with a weight ratio of 8:1:1 in N-methyl pyrrolidone (NMP) to form a homogeneous ink, which was then drop-casted onto a carbon cloth electrode. After drying in a vacuum oven overnight, the carbon cloth with active material on it was then used as the working electrode. A Ag/AgCl electrode and a Pt wire were used as the reference and counter electrode, respectively. For 2-electrode measurement, two pieces of the as-fabricated carbon cloth electrodes with almost the same mass loading were used as the positive and negative electrodes respectively with a porous polymer membrane (Celgrad 3501) as the separator to assemble a coin cell. The capacitance (C, F g$^{-1}$) reported in this work was calculated from CV curves:

$$C = \frac{\int i_{cathodic} dV}{m v \Delta V}$$

where i (mA) is the current, v (mV s$^{-1}$) is the scan rate, m (g) is the mass of the active materials on the single electrodes, and V (V) the potential window.

The energy density (E, Wh kg$^{-1}$) and power density (P, W kg$^{-1}$) were calculated from the GCD curves:

$$E = \frac{i \int V dt}{M \times 3.6}$$

$$P = \frac{E}{t} \times 3600$$

where i (A) is the current, V (V) the cell voltage window, t (s) the discharge time, and M (g) the mass of the active materials on both the positive and negative electrodes.

Results and Discussion

Figures 3A, 3B:
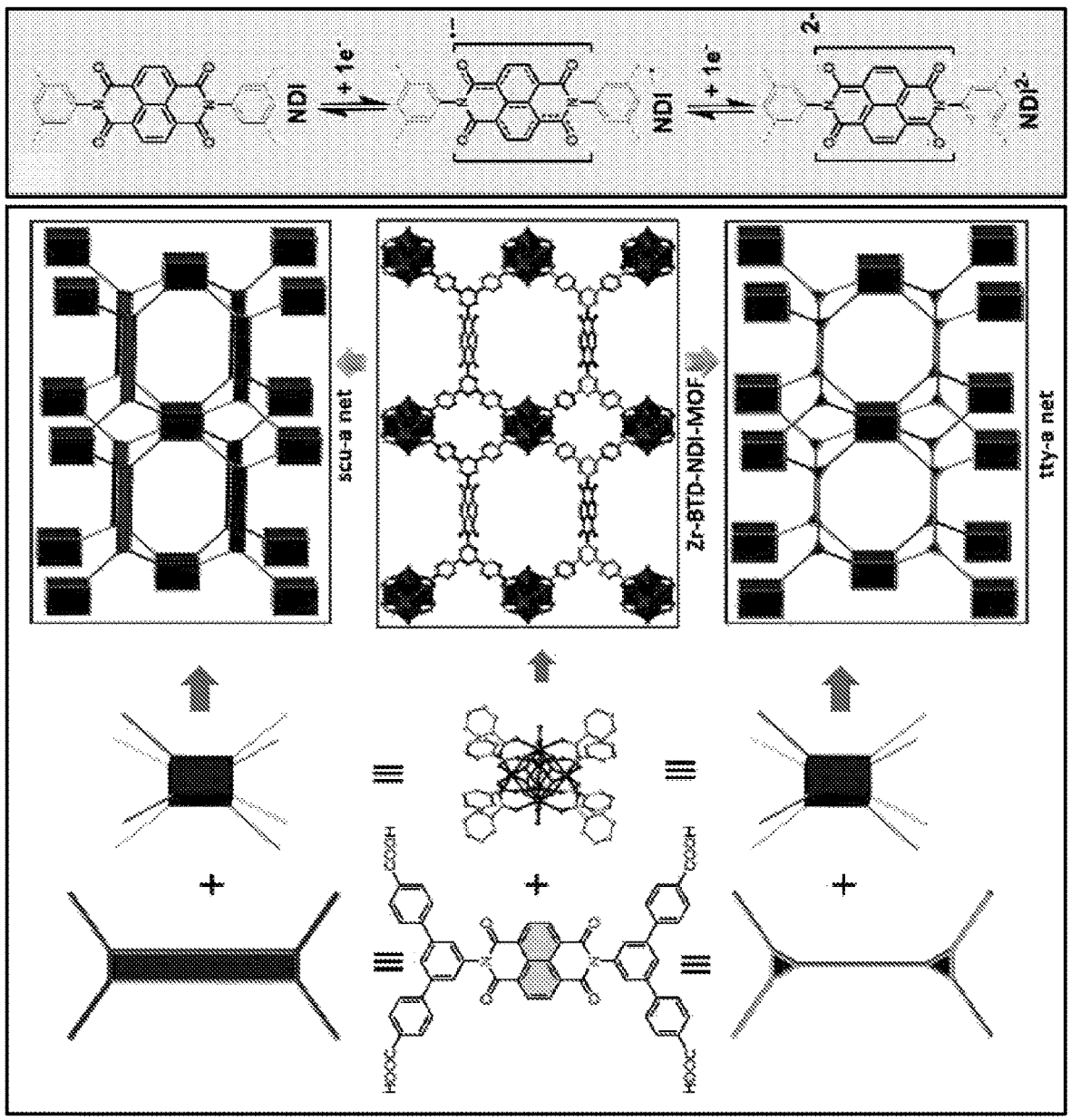
FIGS. 3A-3B illustrate (a) a schematic representation of the synthetic route for Zr-BTD-NDI-MOF showing different topologies that can be obtained and (b) the active core in the NDI linker with the two electron redox process, according to one or more embodiments of the present disclosure.
Figure 4:
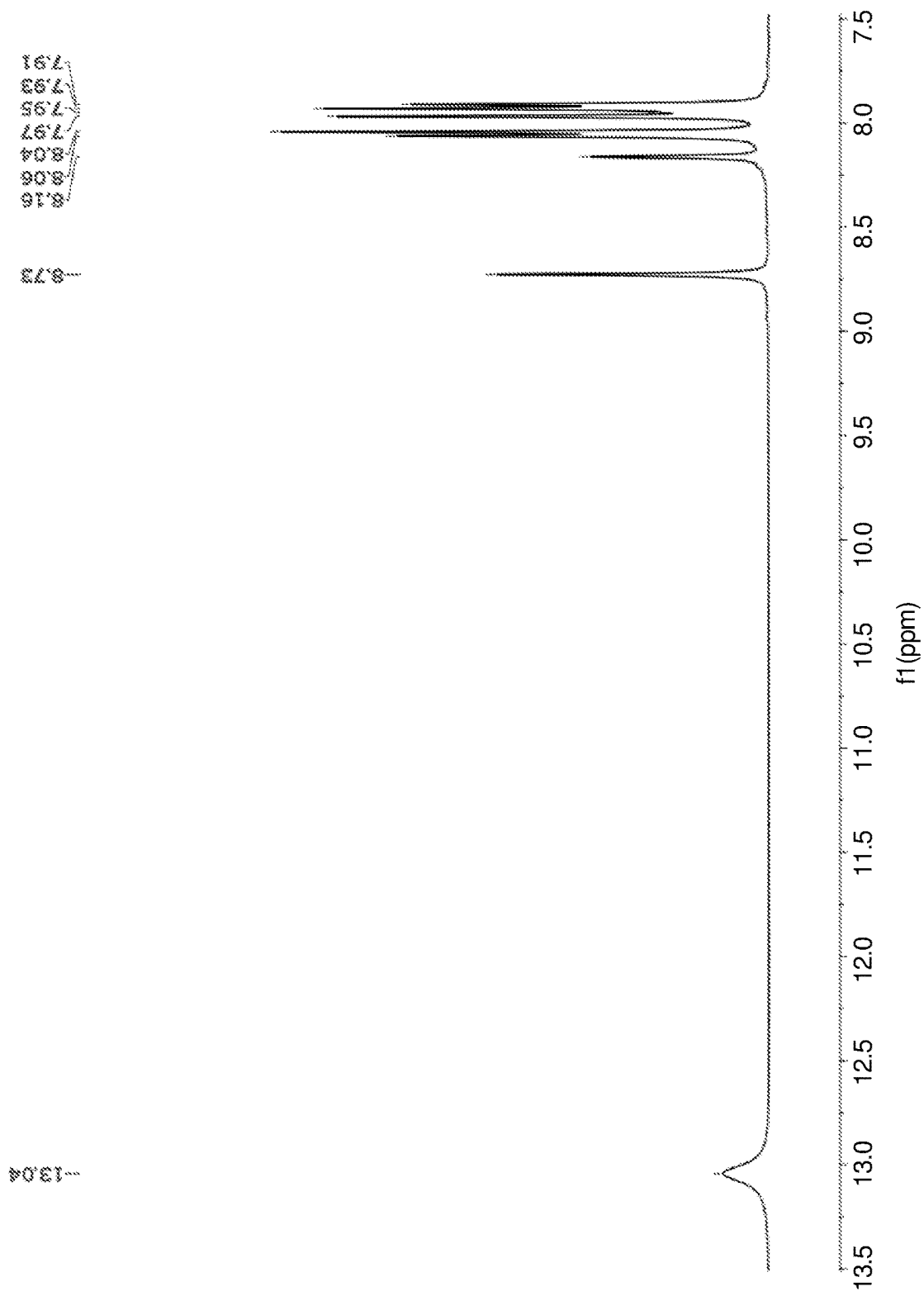
FIG. 4 is a graphical view of $^1$H NMR spectra for the linker showing characteristic peaks, according to one or more embodiments of the present disclosure.
Figure 5:
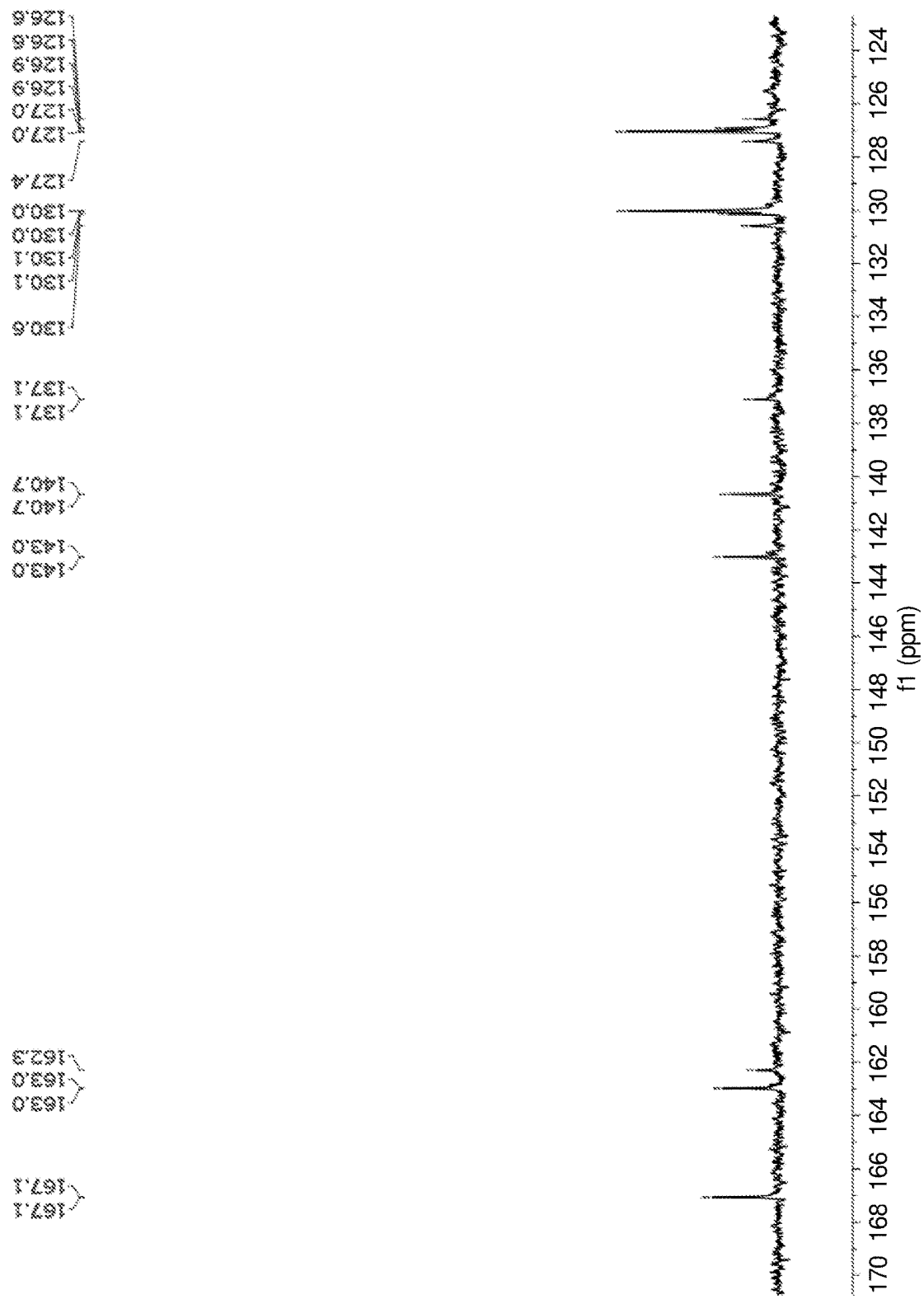
FIG. 5 is a graphical view of $^{13}$C NMR spectra for the linker showing characteristic peaks, according to one or more embodiments of the present disclosure.
Figure 6:
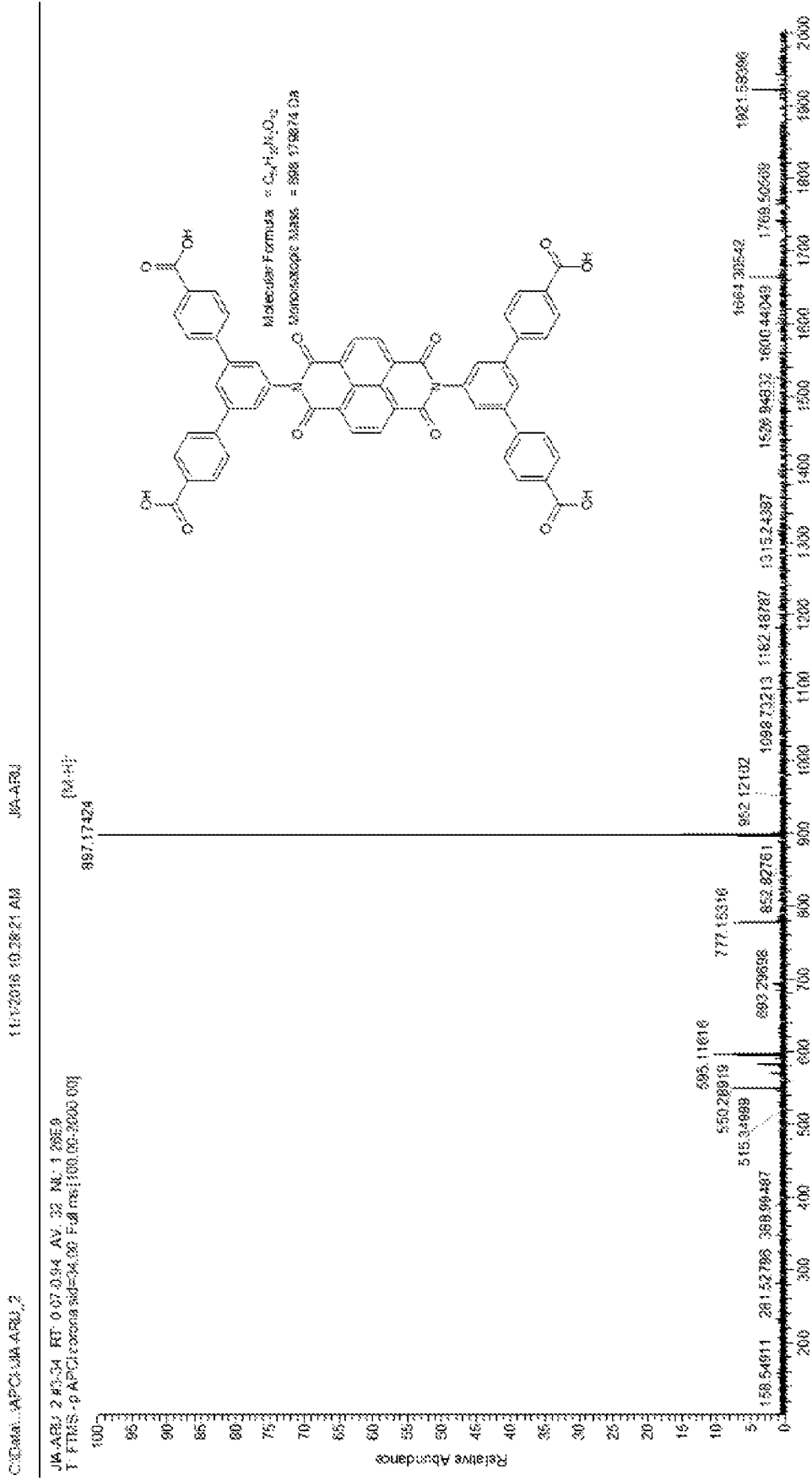
FIG. 6 is a graphical view of mass spectra for the linker showing the exact molecular weight as calculated from the formula, according to one or more embodiments of the present disclosure.

This Example reports the design and synthesis of particular MOFs, where an organic linker having a redox center was strategically incorporated into MOFs and a metal node was judiciously selected to construct a highly porous and stable framework (FIG. 3). The N,N'-bis(terphenyl-4,4''-dicarboxylic acid) naphthalenediimide ($H_4$BTD-NDI) was synthesized and used as the organic linker (Scheme 1; FIGS. 4-6), where naphthalenediimide (NDI) core was the redox-active center, that is known to have two characteristic electron redox processes (FIG. 3b). On the other hand, the $[Zr_6O_4(OH)_8(H_2O)_8]^{8+}$ cluster was chosen as metal node to provide the right connectivity to generate the targeted porous structure with a high chemical stability, which is a key factor for long life cycling stability of the supercapacitor performance. Moreover, the high surface area was expected to increase the double-layer capacitance, and the open framework structures was expected to facilitate ion transport (FIG. 3).

Figure 7:
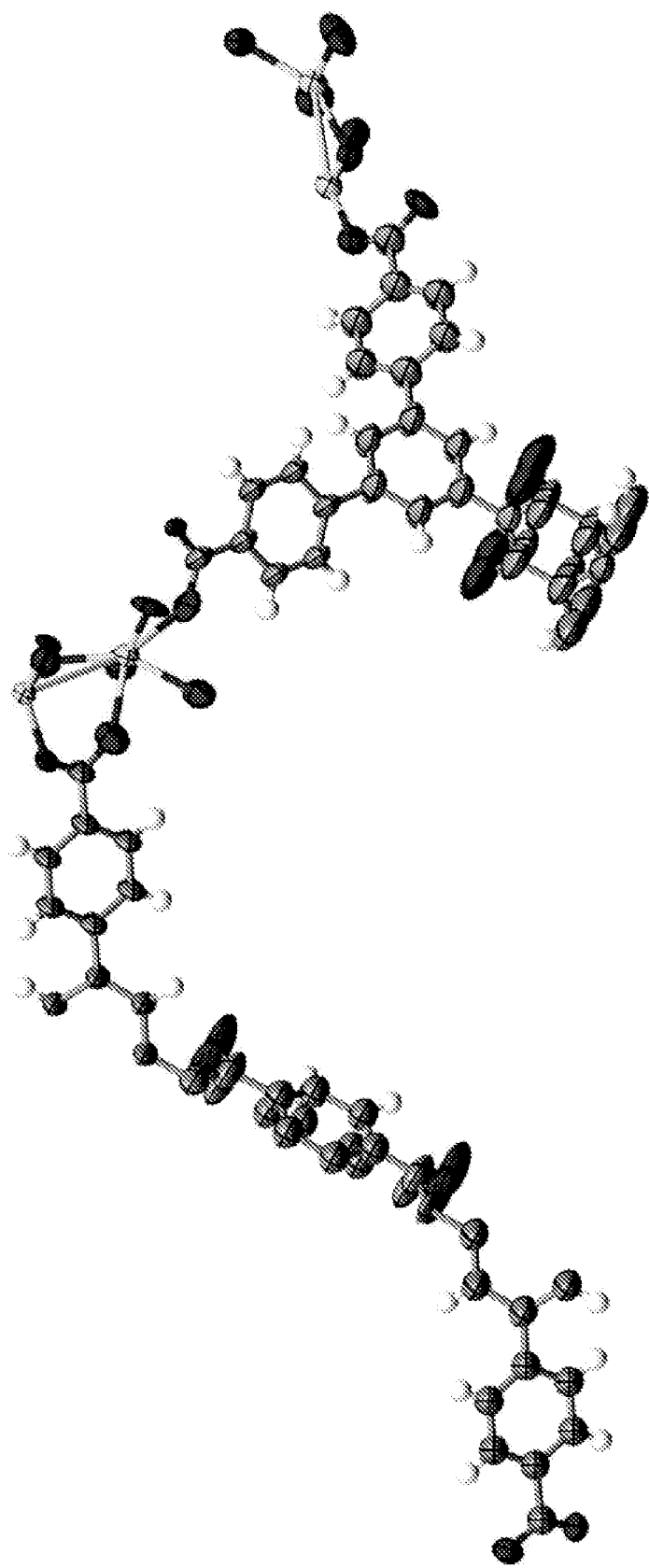
FIG. 7 is a schematic diagram illustrating the structure of Zr-BTD-NDI-MOF depicted in a thermal ellipsoid model with 50% probability, according to one or more embodiments of the present disclosure.

The synthetic conditions for the targeted MOF were optimized to grow single crystals, which was achieved by the reaction of zirconium chloride ($ZrCl_4$) and $H_4$BTD-NDI-linker with excess formic acid and benzoic acid, as reaction modulators, at 120° C., that led to the formation of needle shape Zr-BTD-NDI-MOF single crystals. The single crystal X-ray diffraction studies revealed that the targeted Zr-BTD-NDI-MOF crystallized in the orthorhombic Cmmm space group with a formula unit of (BTD-NDI$_2$Zr$_6$O$_4$(OH)$_4$) and cell parameters of a=20.80; b=34.32; c=24.28 α=β=γ=90 (Table 1). The Zr-BTD-NDI-MOF possessed a neutral framework with octahedral $[Vr_6O_4(OH)_8(H_2O)_8]^{8+}$ clusters, bridged by eight BTD-NDI ligands, while leaving four pairs of terminal $H_2O$ groups at equatorial plane appropriate for further modification (FIG. 3 and FIGS. 7-8). The crystal lattice possessed three types of pores: smaller ones (atom-to-atom separation 14.84×5.06 Å) along the b-axis (b-pores), (13.37×14.84 Å) along the a-axis (a-pores), and larger ones (11.36×26.69 Å) along the c-axis (c-pores). The NDI cores were arranged parallel to the c-pores, which favored the interaction with the incoming guest moieties The topological analysis of the MOF represented the 8-connected hexanuclear Zr(IV) molecular building block (MBB), that can be viewed as a cube secondary building unit (SBU), while the organic ligand can be rationalized as a 4-connected building unit to give (4,8)-c scu-a net or can be viewed as 3-c SBUs resulting in a (3,8)-c derived tty-a net (FIG. 3).

Figure 9A:
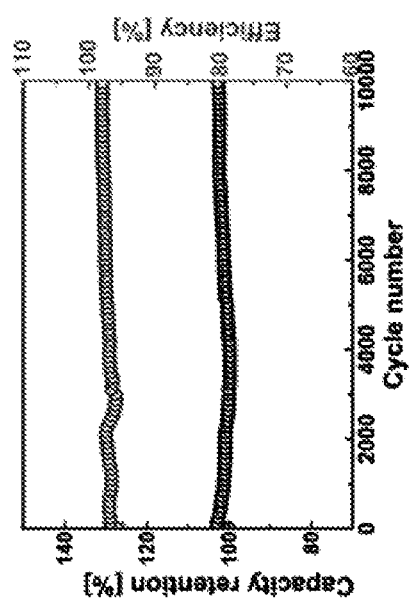
FIGS. 9A-9F relate to Zr-NDI-BPy-MOF symmetric devices and illustrate (a) a graphical view of CV curves measured at different scan rates; (b) a graphical view of GCD curves measured at different current densities; (c) a graphical view of cyclic stability performed at 2 A g$^{-1}$ up to 10,000 cycle; (d) a graphical view of a PXRD pattern comparison before and after the electrochemical measurement; and (e,f) SEM images of the electrode before (e) and after (f) the electrochemical measurement, according to one or more embodiments of the present disclosure.
Figure 9B:
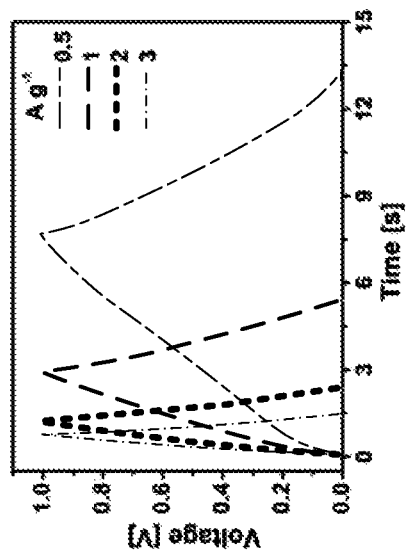
Figure 9C:
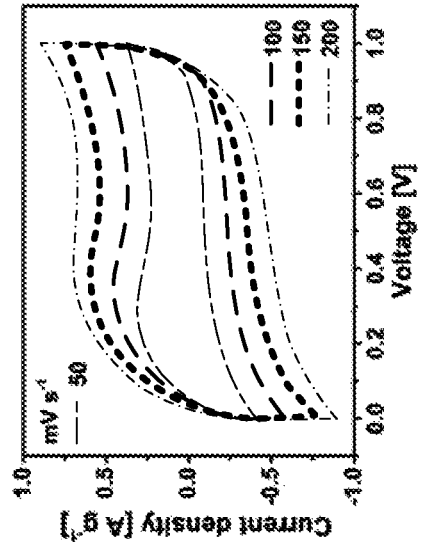
Figure 9D:
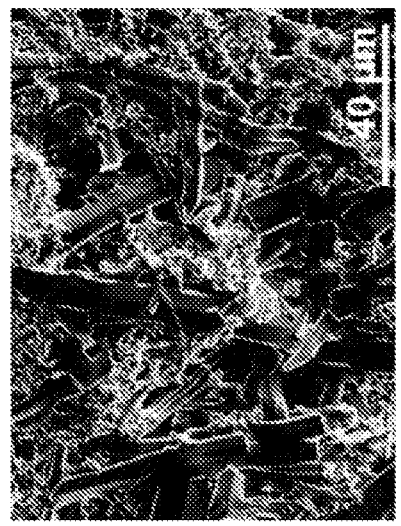
Figure 10:
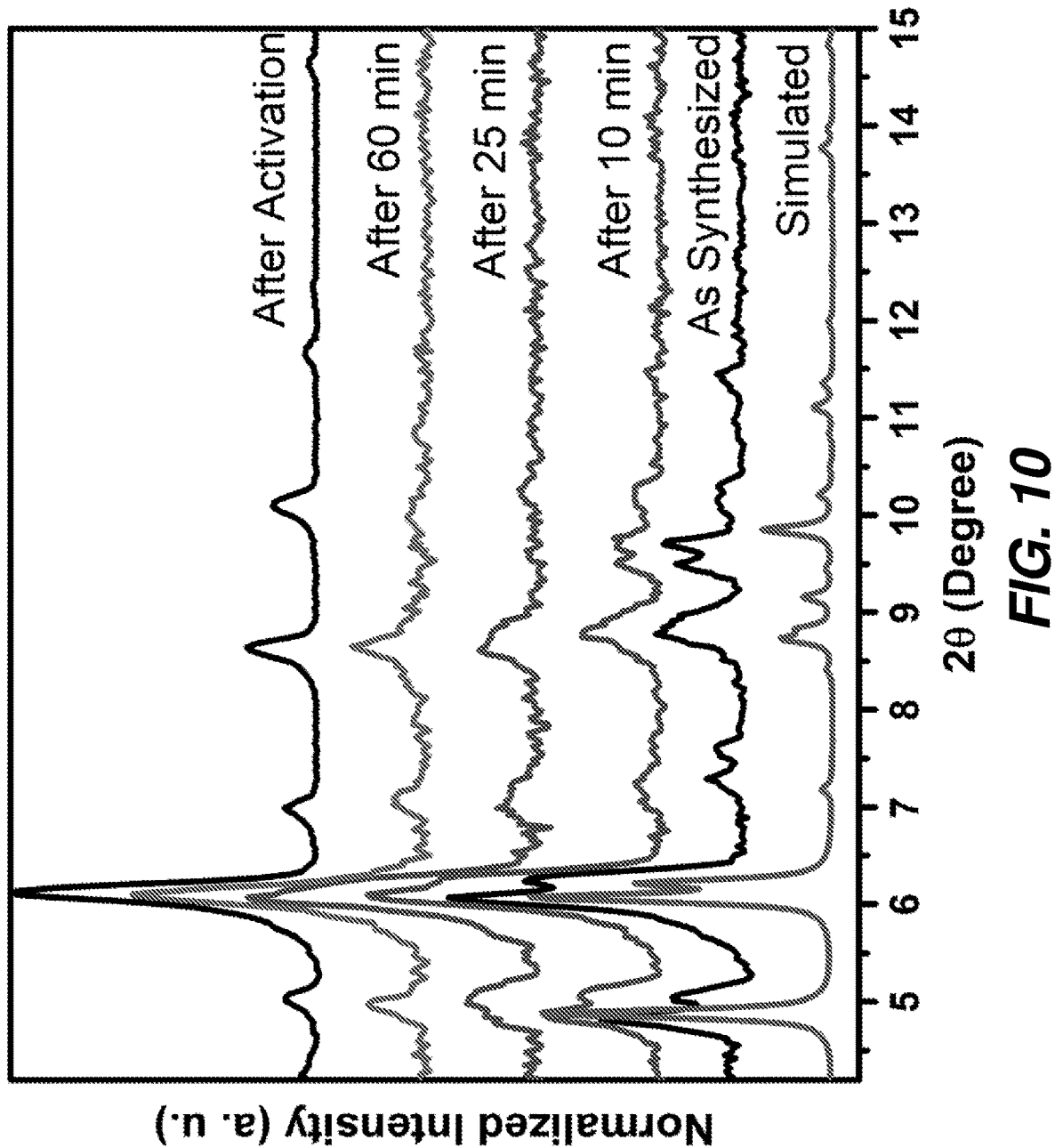
FIG. 10 is a graphical view of a time dependent PXRD pattern for Zr-BTD-NDI-MOF showing the peak shift with removal of the trapped solvent, according to one or more embodiments of the present disclosure.
Figure 11:
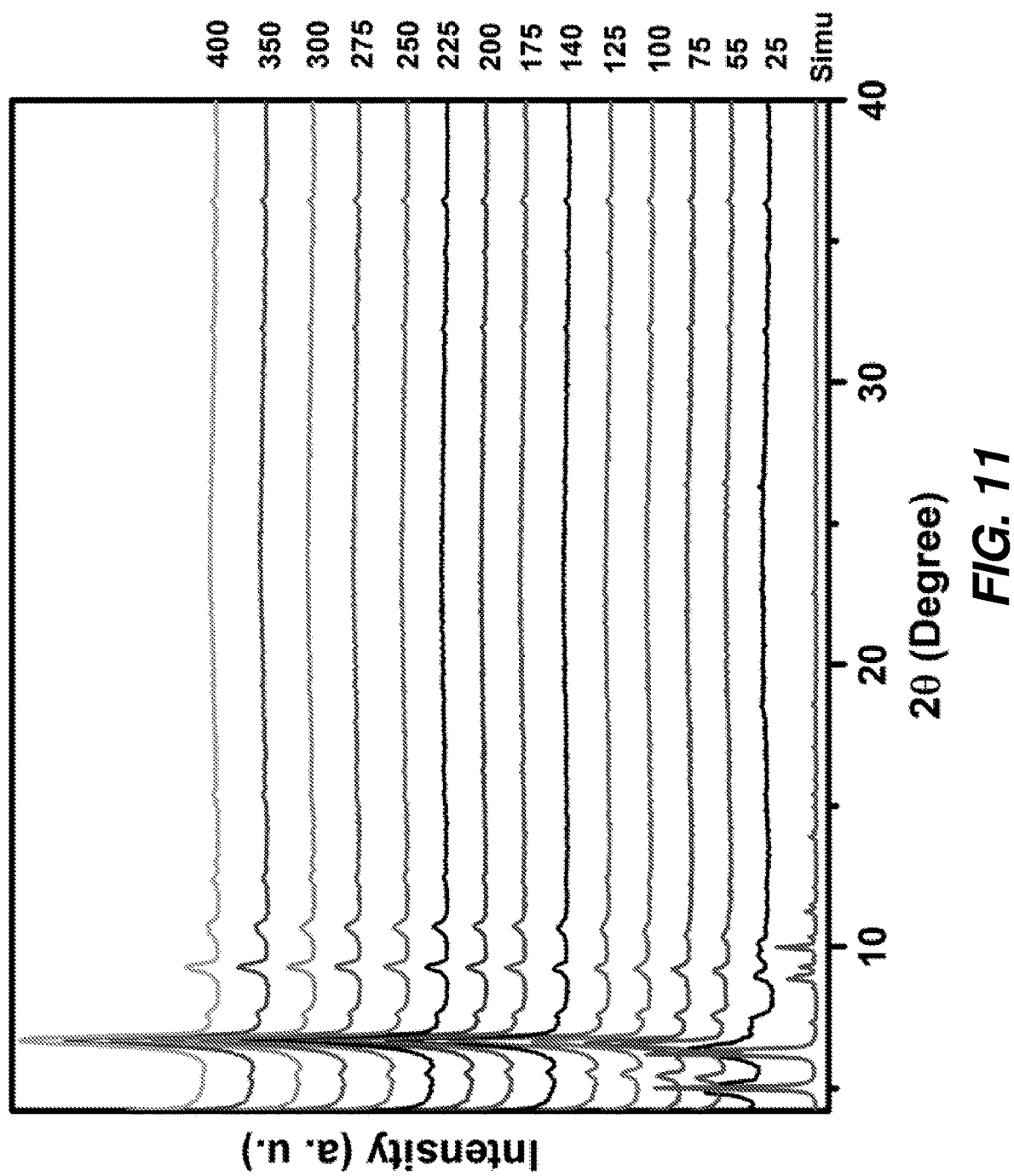
FIG. 11 is a graphical view of a temperature dependent PXRD pattern for Zr-BTD-NDI-MOF showing the thermal stability up to 400° C., according to one or more embodiments of the present disclosure.

The phase purity of the Zr-BTD-NDI-MOF was confirmed by matching the powder X-ray diffraction (PXRD) pattern of the experimental and simulated pattern obtained from the crystal structure (FIG. 9d). Interestingly, a phase change was observed from the PXRD pattern upon activation or solvent exchange of the sample (FIG. 10). This phase change was attributed to the flexibility of the framework upon solvent removal. This was confirmed from variable temperature PXRD (VT-PXRD) (FIG. 11), which shows the shift of the PXRD peak at 4.7 to 5.1 degrees. The permanent porosity of the Zr-BTD-NDI-MOF was confirmed by surface area analysis from the Ar sorption isotherm measured at 78 K and 1 bar. The Zr-BTD-NDI-MOF showed a surface area around 810 m$^2$ g$^{-1}$. However, the framework did not show the optimum pore volume compared to the calculated pore volume, which was mainly due to the flexible nature of this framework. The framework flexibility was also confirmed from the shape of the isotherm, where, a step was obtained at 0.25 bar relative pressure (p/p$_o$) (FIG. 12a).

Figure 15A:
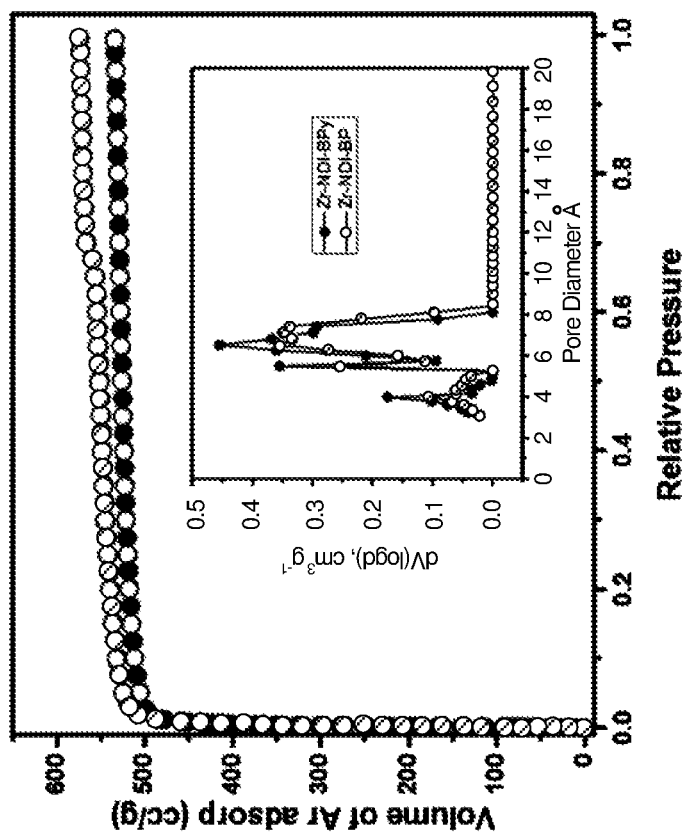
FIGS. 15A-15B are Ar adsorption isotherms for (a) Zr-BTD-NDI and pore size distribution plot in inset and (b) Zr-BTD-NDI-BP and Zr-BTD-NDI-BPy, with graphical views of pore size distribution provided in the insets, according to one or more embodiments of the present disclosure.
Figure 16:
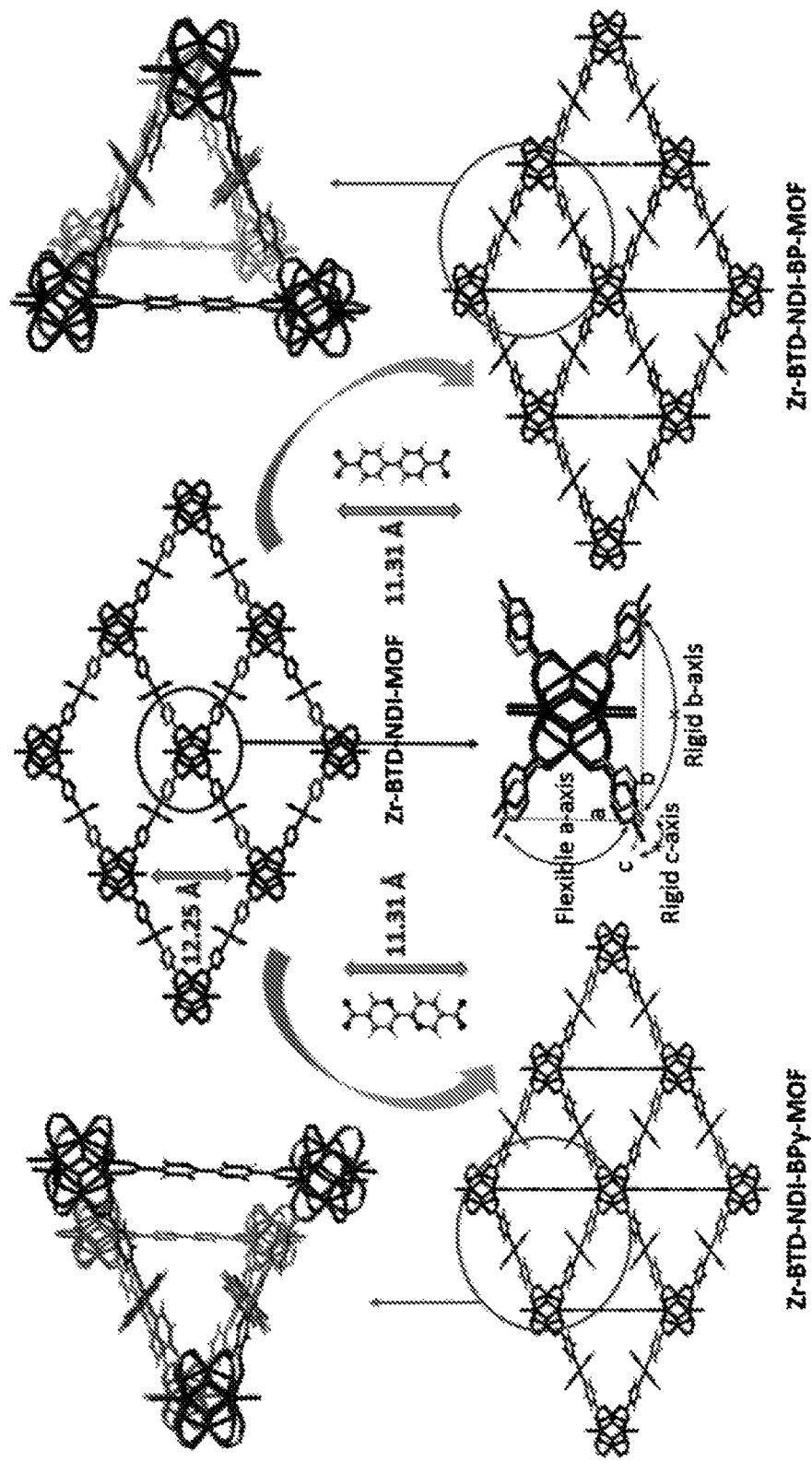
FIG. 16 is a schematic diagram of the structure of the Zr-BTD-NDI-MOF and the insertion of two organic pillars, according to one or more embodiments of the present disclosure.

Electrochemical measurements were carried out on the Zr-BTD-NDI-MOF using a three-electrode configuration in 1 M H$_2$SO$_4$ supporting electrolyte. The working electrode was prepared by drop-casting a homogeneous ink of MOF, carbon black, and polyvinylidene fluoride (PVDF) binder (8:1:1 in weight ratio) onto a carbon cloth (CC) electrode (the typical mass loading was around 1.5-2 mg cm$^{-2}$). A Ag/AgCl electrode and a Pt wire were used as the reference and counter electrode, respectively. FIG. 13a shows the CV curve (type 1) collected at a scan rate of 50 mV s$^{-1}$. Due to the high surface area of the Zr-BTD-NDI-MOF, it was expected to show electrochemical double layer capacitance (EDLC) due to the adsorption of ions during electrochemical process. Moreover, the NDI moieties within the Zr-BTD-NDI-MOF underwent reversible redox processes, which exhibited a well-defined electrochemical response. Indeed, the CV curve exhibited a quasi-rectangular shape with distinct redox peaks, indicative of typical hybrid capacitive behavior. Specifically, two anodic peaks located at about 0.4 and 0.6 V vs Ag/AgCl (FIG. 15a) were observed, corresponding to the two-step redox reaction as expected for the NDI core (see inset of FIG. 3). The nonlinear galvanostatic charge-discharge (GCD) profile further suggested the faradaic process (FIG. 13b). Overall, the combination of EDLC and pseudo-capacitive behavior was observed. The capacitance was calculated from the CV curves and the Zr-BTD-NDI-MOF electrode delivered a high capacitance of 16.8 F g$^{-1}$ at a scan rate of 10 mV s$^{-1}$. An interesting feature of the Zr-BTD-NDI-MOF was the flexible behavior, which was driven by the removal/uptake of solvent. The flexibility of the Zr-BTD-NDI-MOF may affect performance as a supercapacitor, since it can lower the surface area. Careful inspection of the crystal structure showed that each Zr-cluster contained eight carboxylates from eight linkers and these carboxylates were rigid along the b- and c-axis and elastic along the a-axis. As a result, the framework became flexible along the a-axis and upon removal of solvent a partial rupture of the framework occurred. Also each Zr-cluster contained eight water molecules, among them, four water molecules faced the a-axis and the other four water molecule faced along the c-axis (FIG. 16). The open sites offered the opportunity to install another linker through the a-axis by replacing the water molecules. Thus the flexible framework of the Zr-BTD-NDI-MOF can be transformed into a more rigid framework via this linker installation (FIG. 16).

Figure 12:
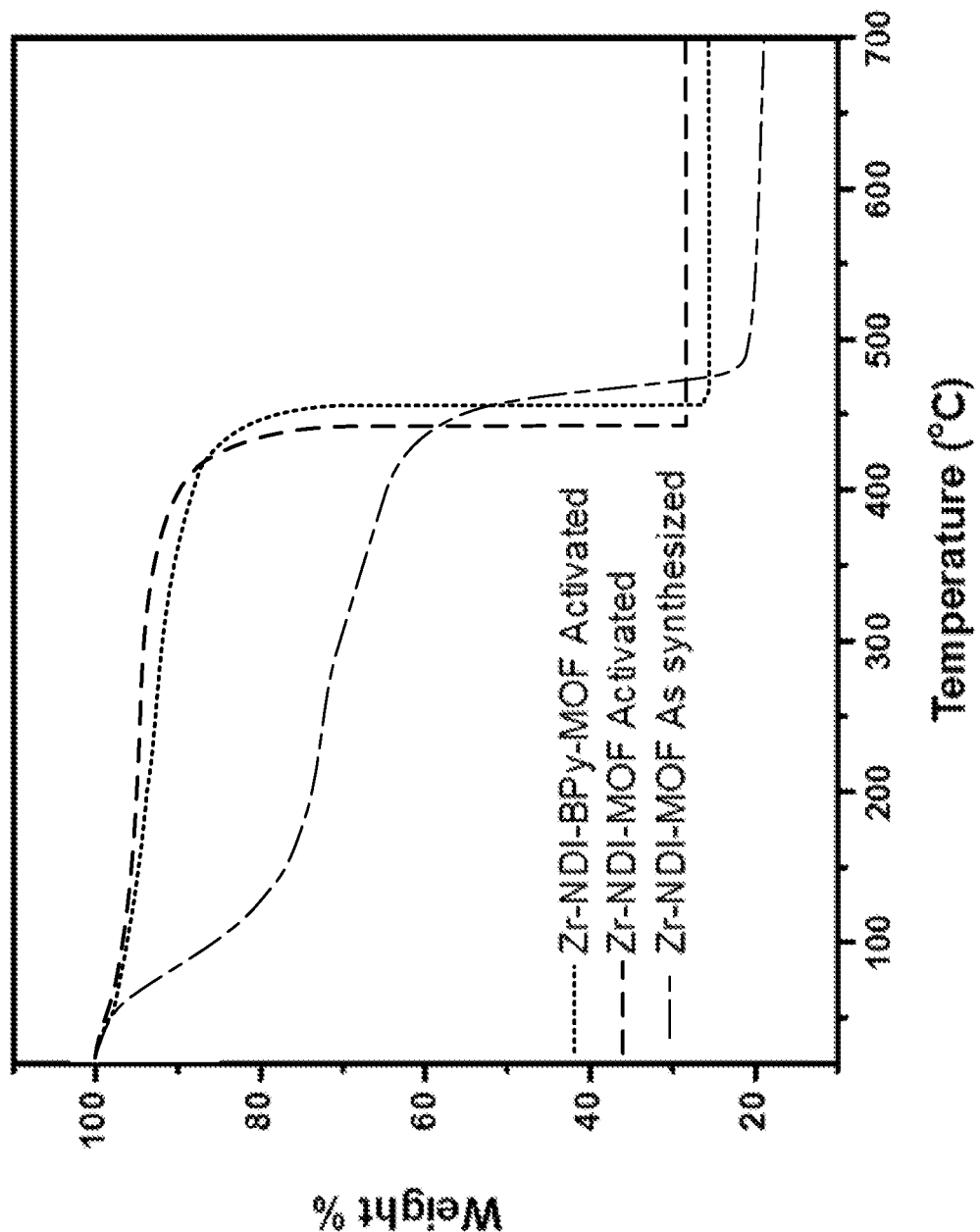
FIG. 12 is a graphical view of TGA plots of the synthesized MOFs showing their thermal stability, according to one or more embodiments of the present disclosure.
Figure 14:
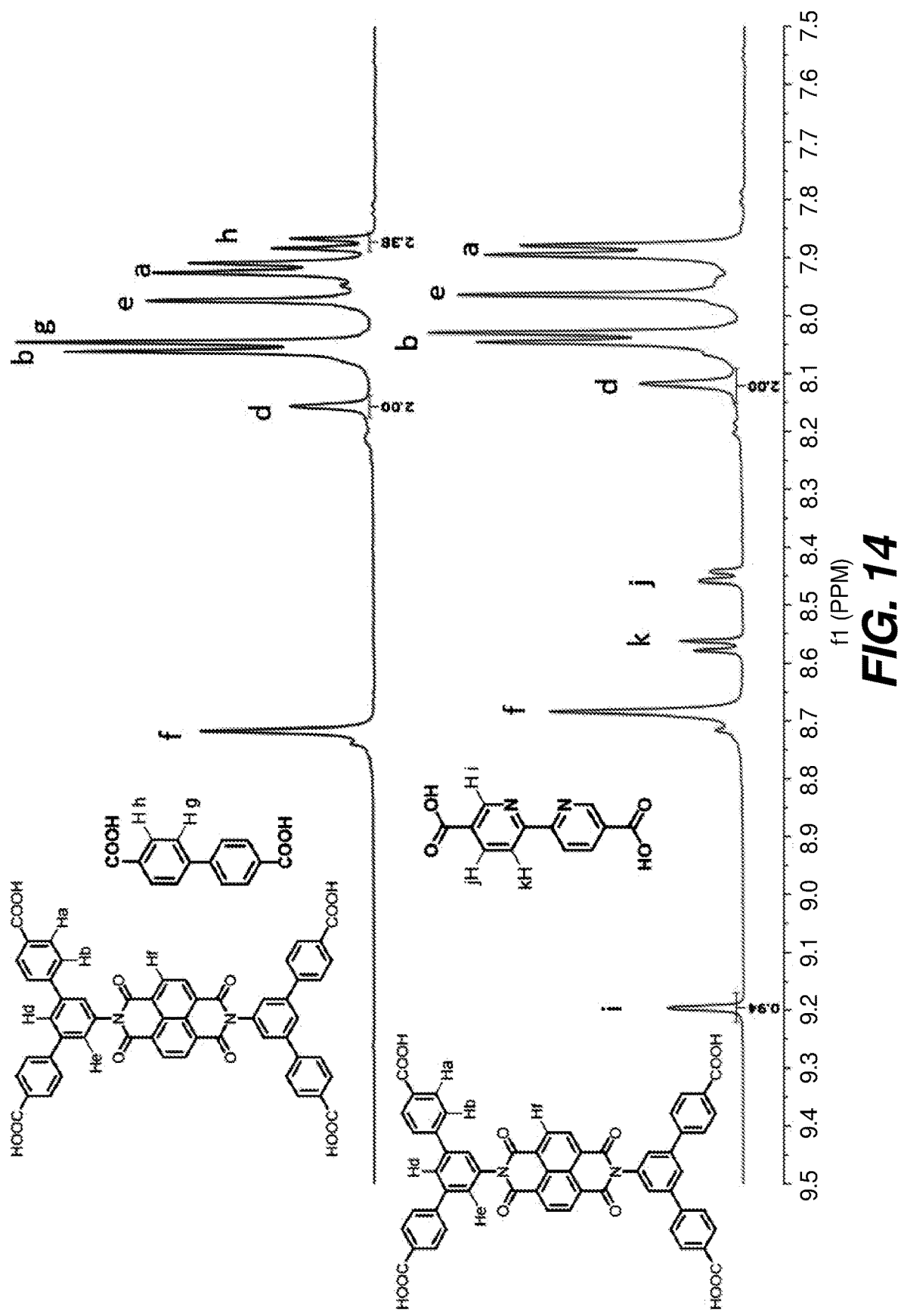
FIG. 14 is a graphical view of 1H NMR spectra for the pillar installed MOFs (for $^1$H NMR analysis of Zr-BTD-NDI-BP and Zr-BTD-NDI-BPy-MOF, the samples (around 5 mg) were digested by 12 M HCl aqueous solution and dried in a 100° C. oven; the solid was dissolved in about 0.5 mL d$^6$-DMSO), according to one or more embodiments of the present disclosure.
Figure 17:
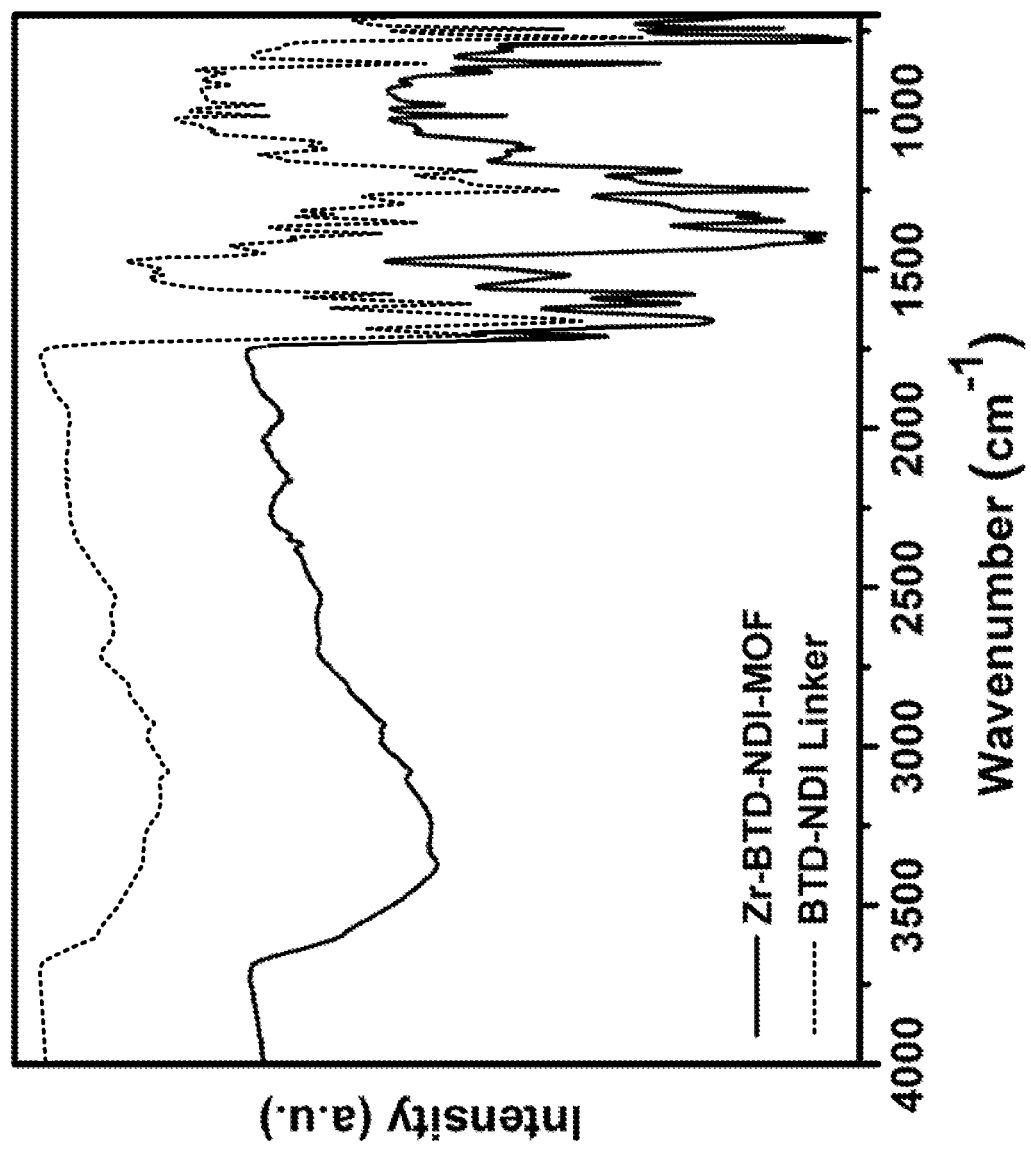
FIG. 17 is a graphical view showing a comparison of FT-IR spectra of the linker and Zr-BTD-NDI-MOF, according to one or more embodiments of the present disclosure.

The post-synthetic linker installation was carried out using 4,4-biphenyldicarboxylic acid (BP). The reason behind the selection of BP was that the distance between the two opposite water molecules along the c-axis was about 12.36 Å, which fit perfectly with the length of the BP (11.1 Å). The post-synthetic linker installation was performed by immersing the solvent exchanged crystals of the Zr-BTD-NDI-MOFs into the DMF solution of BP at 85° C. for one day. The amount of linker installed in the framework was estimated via nuclear magnetic resonance (NMR) spectra of the digested MOF in HCl (FIG. 6). It was observed that the installed linkers occupied about 85% of the available binding sites. The post-installation of the linkers was also confirmed by other techniques like (thermal gravimetrical analysis (TGA), Infrared spectroscopy (IR), PXRD, elemental analysis, and surface area analysis (FIGS. 12, 15, 17).

Figure 15B:
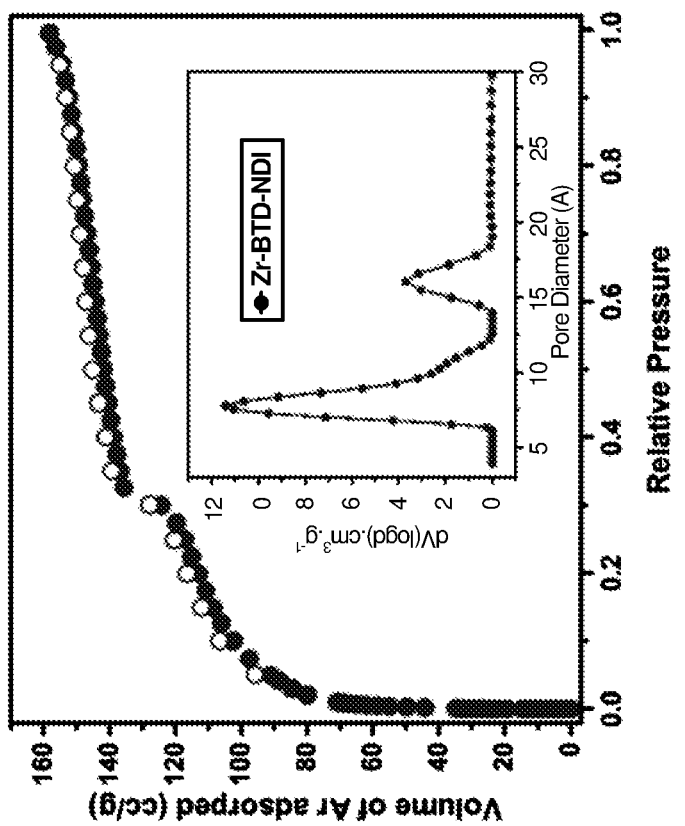
Figure 18:
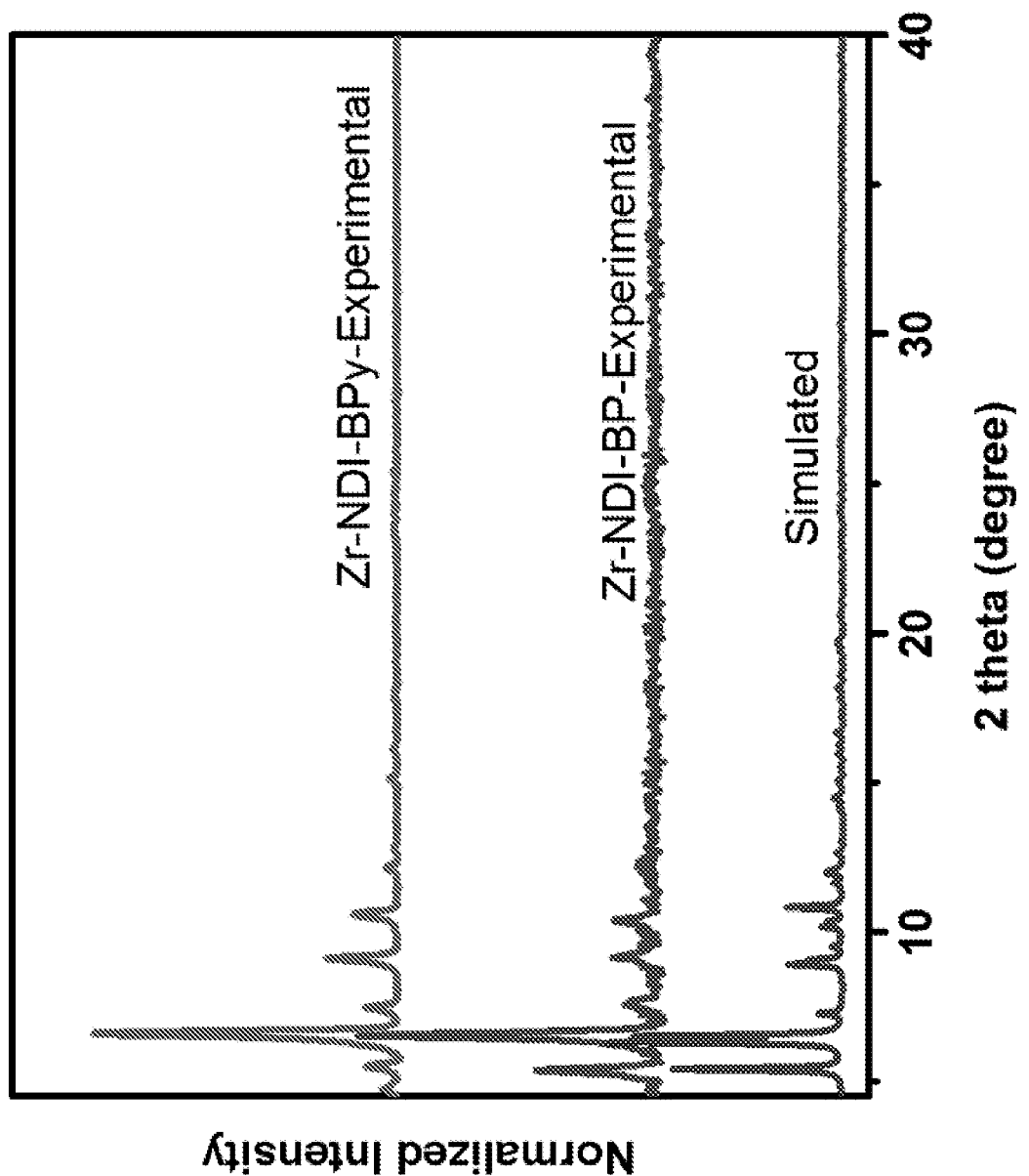
FIG. 18 is a graphical view showing a comparison of the PXRD pattern of bulk Zr-BTD-NDI-BP-MOF and Zr-BTD-NDI-BPy-MOF crystal with their simulated pattern, according to one or more embodiments of the present disclosure.
Figure 19:
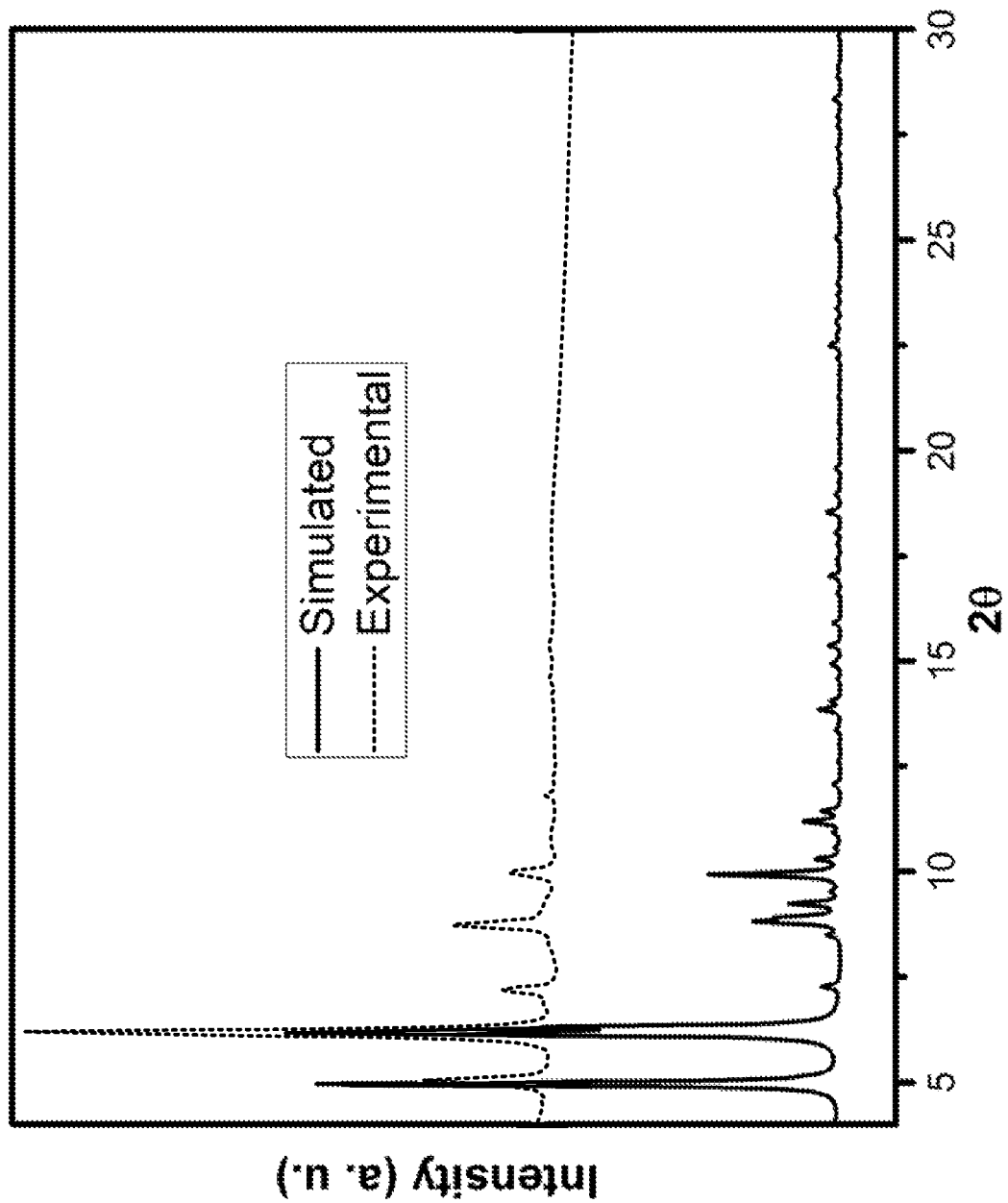
FIG. 19 is a graphical view showing a comparison of PXRD pattern of experimental with simulated for Zr-BTD-NDI-MOF, according to one or more embodiments of the present disclosure.
Figure 20A:
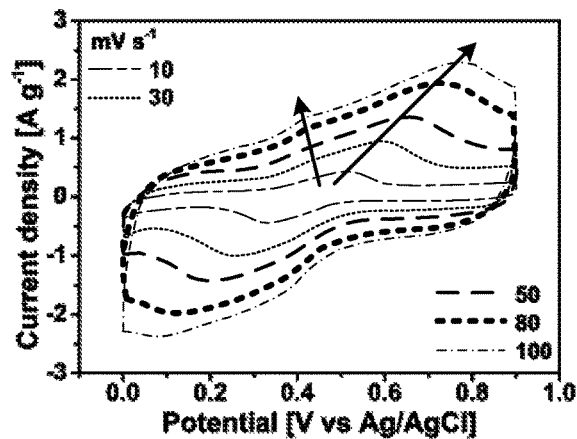
FIGS. 20A-20F are graphical views of (a,c,e) CV curves and (b,d,f) CD curves recorded at different scan rates and current densities, respectively, for (a,b) Zr-BTD-NDI-MOF, (c,d) Zr-BTD-NDI-BP-MOF, and (e,f) Zr-BTD-NDI-BPy-MOF in three-electrode measurements using 1 M $H_2SO_4$ as electrolyte, according to one or more embodiments of the present disclosure.
Figure 20B:
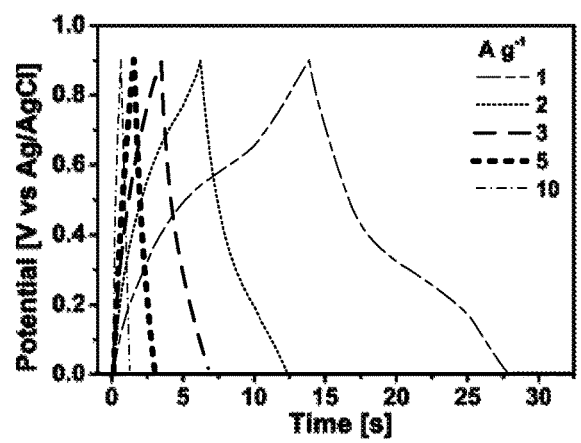
Figure 20C:
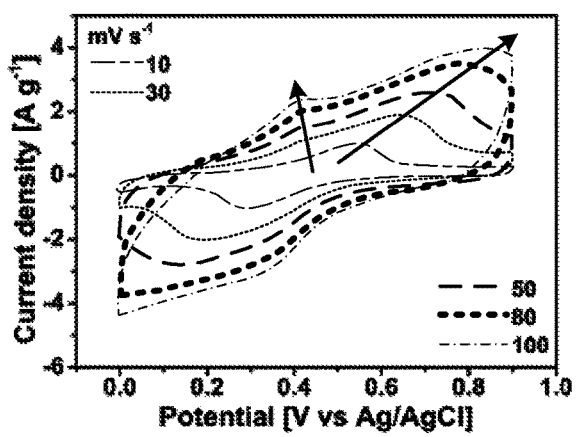
Figure 20D:
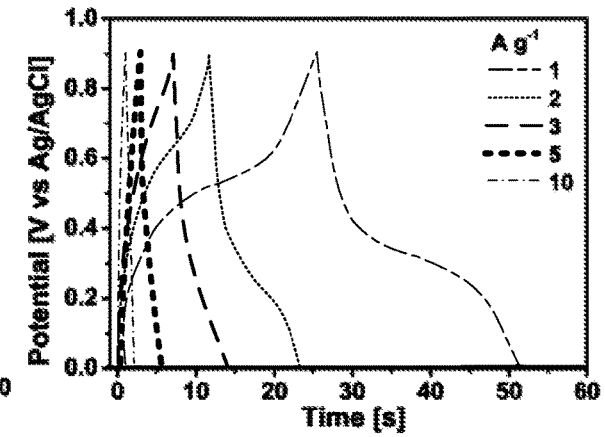
Figure 20E:
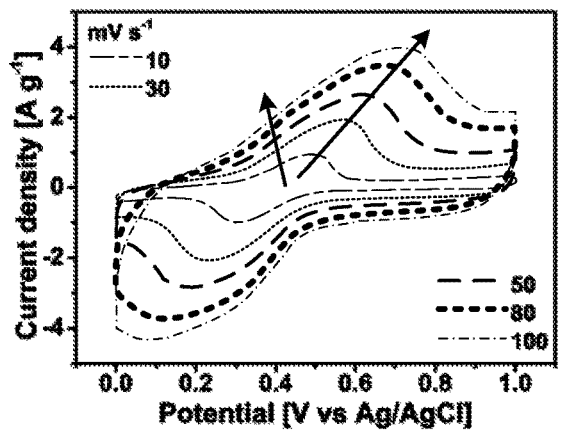
Figure 20F:
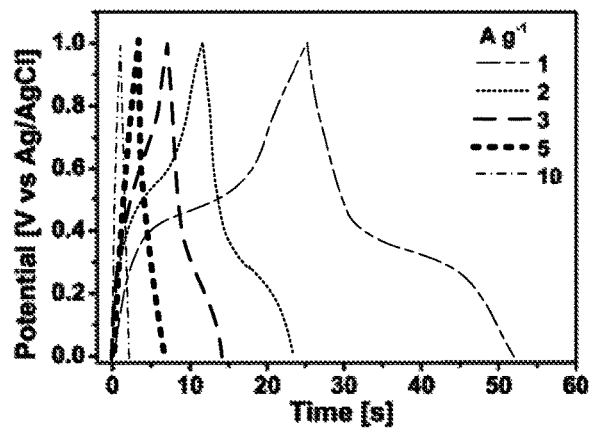
Figure 21:
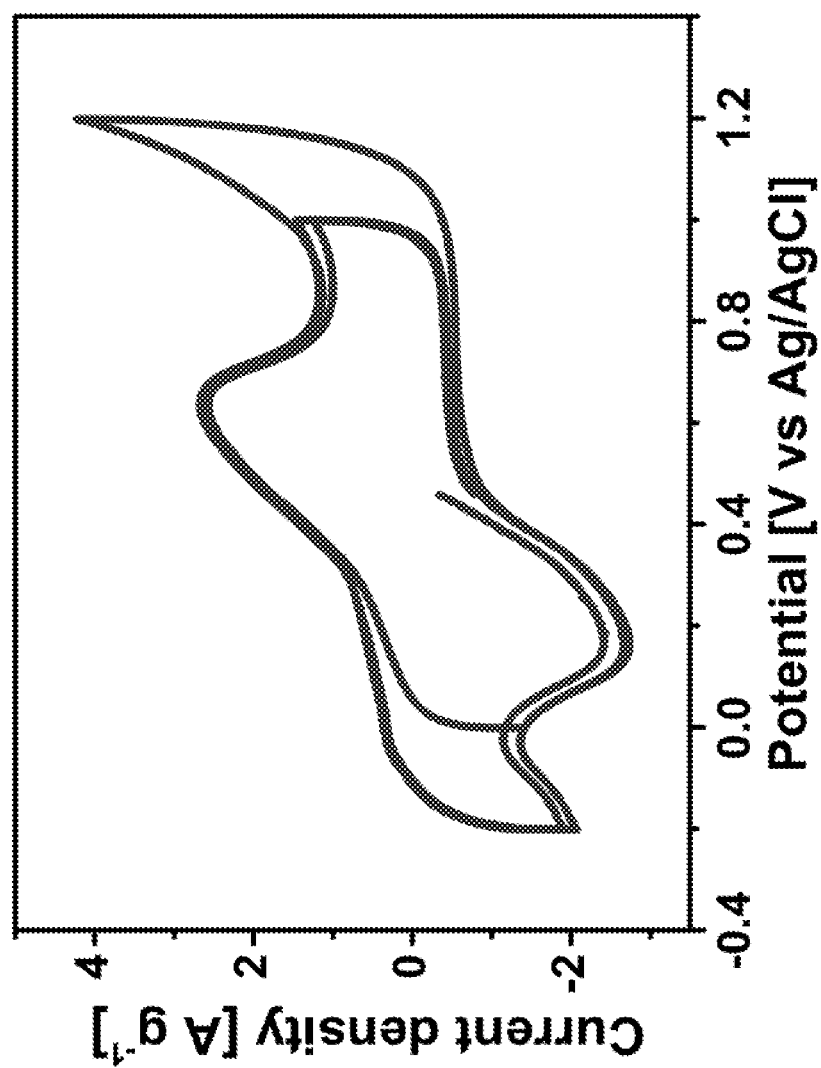
FIG. 21 is a graphical view of the current density versus potential for determination of the potential window of the Zr-BTD-NDI-BPy-MOF, according to one or more embodiments of the present disclosure.

The obtained Zr-NDI-BP-MOF was fully characterized with PXRD (FIG. 18), which confirmed the presence of the expected structure and that the structure maintained its crystallinity. The simulated PXRD pattern of the linker installed MOFs (Zr-BTD-NDI-BP-MOF) was obtained from the optimized structure using materials studio software. The experimental PXRD pattern for the linker installed MOFs were in good agreement with the simulated pattern (FIG. 18). In addition, the Ar sorption showed an enhancement in the surface area, which became 1920 m$^2$/g after installation (FIG. 15b). The increase in surface area was obtained due to the maintained pore opening by the installed linkers. The Ar isotherm also showed no more steps at higher partial pressure, which confirmed the microporous framework structure (FIG. 15b) and rigidity of the new MOF. Such a large increase in surface area was expected to further boost the supercapacitor performance Indeed, the CV area of the Zr-BTD-NDI-BP-MOF (type 2 in FIG. 13a) significantly increased as compared to that of Zr-BTD-NDI-MOF. Notae that for both MOFs, the CV curves showed similar shapes and redox peaks (FIG. 20). These results suggested that the capacitance can be greatly enhanced by simply installing the BP linker. The GCD curve again confirmed such enhancement (FIG. 13b). The capacitance of the Zr-BTD-NDI-BP-MOF was calculated to be 32.8 F g$^{-1}$ (FIG. 13c), two times that of Zr-BTD-NDI-MOF, which was in good agreement with the enhancement of the surface area. These encouraging results led to efforts to improve the performance of this MOF by replacing the BP pillar with a more nitrogen rich pillar, i.e., 2,2'-bipyridine-4,4'-dicarboxylic acid (BPy). The installation of the BPy pillar was performed using the same procedure for the BP pillar and was fully characterized using the same techniques, which confirmed the formation of the targeted structure and the enhancement in the porosity (1820 m$^2$ g$^{-1}$) in comparison to the pristine Zr-BTD-NDI-MOF. The CV curve of this new rigid Zr-BTD-NDI-BPy-MOF (type 3 in FIG. 13a, also see FIG. 15) exhibited a shape similar to Zr-BTD-NDI-BP-MOF (type 2) and Zr-BTD-NDI-MOF (type 1). The CV area did not show significant increase compared to that of Zr-BTD-NDI-BP-MOF. However, the potential window was found to be able to extend to 1.0 V (FIG. 21), which indicated the oxygen evolution reaction on Zr-BTD-NDI-BPy-MOF was restricted to some degree. Such widened potential window was preferred as it can improve the energy and power density of the devices. The pronounced potential plateaus observed in the GCD profile (FIG. 13b) were related to the faradaic reactions of the NDI core, which was in agreement with the CV measurements. The capacitance was further estimated from CV curves and the Zr-BTD-NDI-BPy-MOF delivered a capacitance of 30.7 F g$^{-1}$ at 10 mV s$^{-1}$ (FIG. 13c), slightly lower than that of Zr-BTD-NDI-BP-MOF, but significantly higher than that of pristine Zr-BTD-NDI-MOF (16.8 F g$^{-1}$ at 10 mV s$^{-1}$). These results further confirmed the efficacy of the strategy of using BPy to greatly boost the electrochemical performance. All 3 types of MOF materials were highly stable during measurements in 1 M H$_2$SO$_4$(FIG. 13d). The performance did not show significant decay for at least 5000 cycles even under a relatively high current density (5 A g$^{-1}$).

Figure 9E:
Figure 9F:
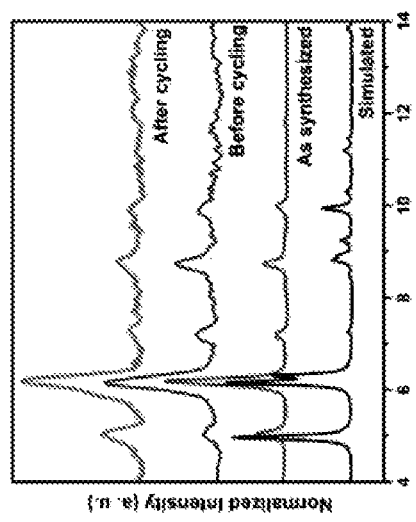
Figure 22C:
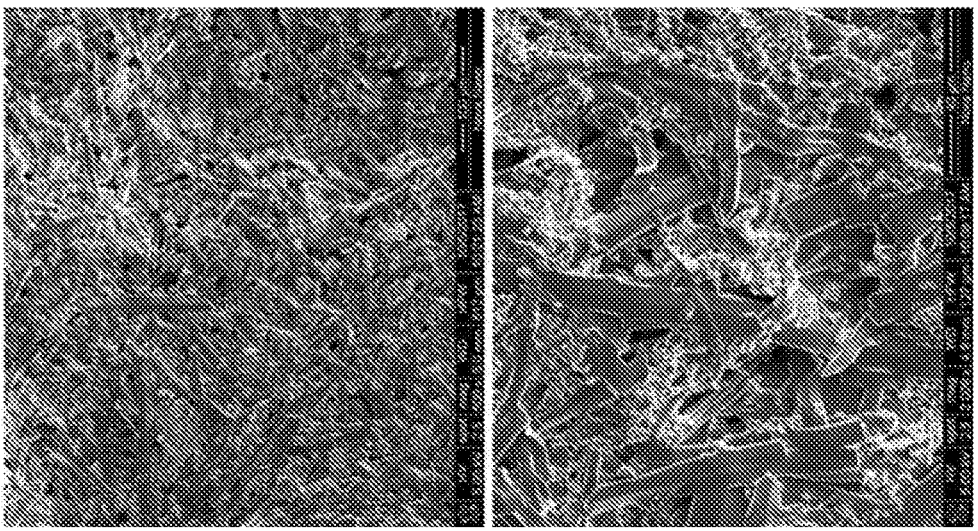
FIGS. 22A-22C illustrate low- (top panel) and high-magnification (bottom panel) SEM images of (a) carbon cloth (CC) electrode, (b) Zr-BTD-NDI-BPy-MOF on CC electrode, and (c) MOF electrode after cycling, according to one or more embodiments of the present disclosure.
Figure 22B:
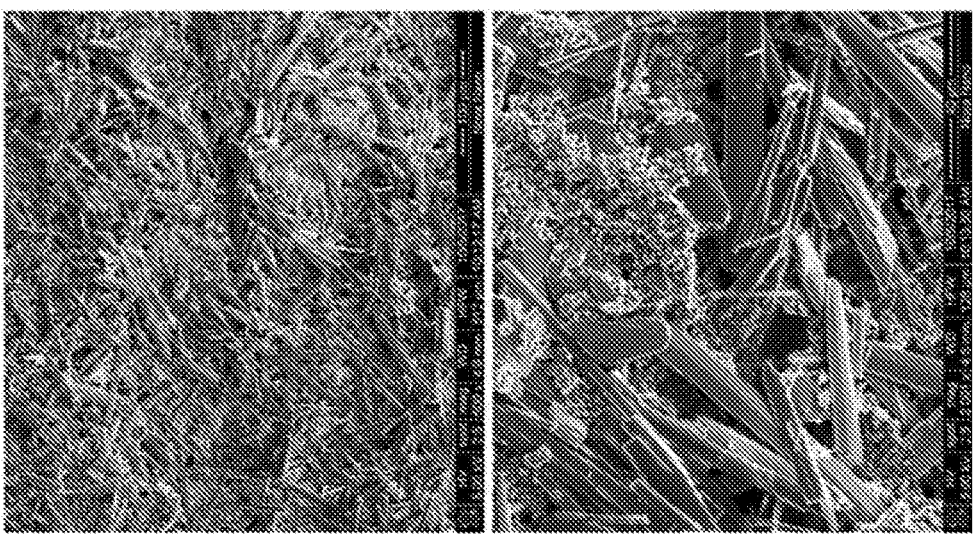
Figure 22A:
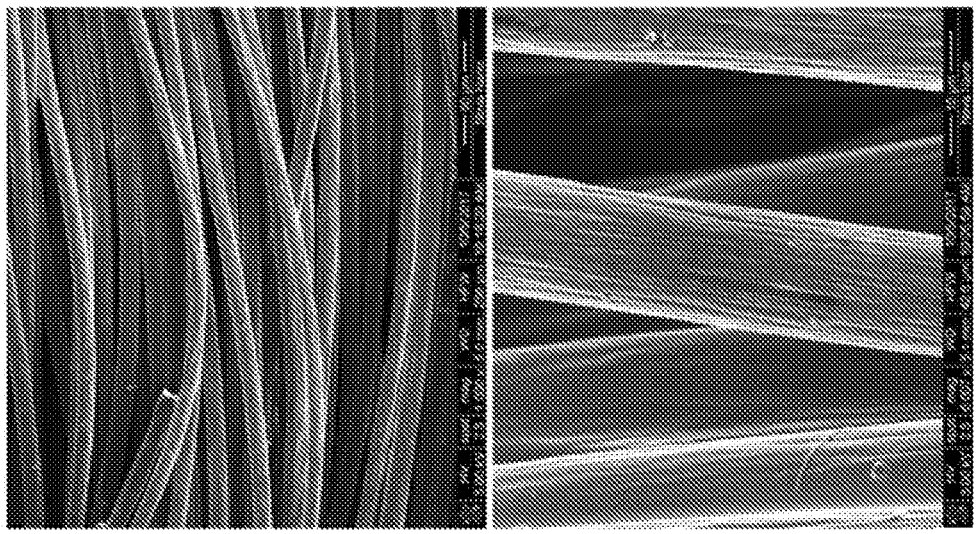

Encouraged by these promising results, the Zr-BTD-NDI-BPy-MOF was further investigated by constructing a symmetrical two-electrode device using two nearly identical electrodes. The preparation of the Zr-BTD-NDI-BPy-MOF and the graphite electrodes was performed in the same way as in the 3-electrode measurements, as the positive and negative electrodes, respectively. The electrolyte used in these measurements was 1 M $H_2SO_4$ and based on the three electrode measurements, these devices were tested in voltage window of 0-1.0 V. FIG. 9a shows the typical CVs collected at different scan rates, which exhibited quasi-rectangular mirror-symmetric shape even at high scan rates (e.g. 200 mV s$^{-1}$), indicating highly reversible charge/discharge response of the device. The triangular symmetric GCD curves indicated a high columbic efficiency. The cell capacitance was calculated based on the CV curves and the devices can deliver a capacitance of 5.7 F g$^{-1}$ at 10 mV s$^{-1}$. The scan rate dependence of capacitance is shown in FIG. 21a. This capacity was achieved in aqueous media with a voltage window of 0.0-1.0 V and the capacitance was higher than most of the reported values achieved in much more expensive organic electrolytes for MOF materials (see Table 2, note here areal capacitance was used as to compare with other MOFs reported in literature). FIG. 9c shows the cyclic stability of our Zr-BTD-NDI-BPy-MOF in 1 M $H_2SO_4$ for up to 10,000 cycles. The MOF based devices showed the capacity retention of 99.9% after 10K cycles, while most of the reported MOF based supercapacitors retained less than 80% of initial capacitance after 10K cycles. This was due to the presence of rigid pillars which gave the structure more stability and hindered the structural collapse during charge/discharge process. The idea of structural retention was also supported by the ex-situ XRD and SEM characterization, where no significant change was observed in the XRD pattern before and after 10K cycles of charge/discharge process (FIG. 9d). The SEM images of the electrodes before and after 10K cycles of charge/discharge process confirmed that the overall morphology remained the same and was not destroyed during the electrochemical cycling (FIGS. 9e-9f and FIG. 22).

TABLE 2

Comparison of the Zr-BTD-NDI-BPy-MOF and other reported MOFs

| Material | Area capacitance (mF cm$^{-2}$) | Electrolyte | Voltage window (V) | Cycle number | Capacity retention (%) |
|---|---|---|---|---|---|
| Zr-ETD-NDI-BPy | 5.48 | 1M $H_2SO_4$ | 0.0-1.0 | 10,000 | 99.9 |
| nMTV-MOF-5-AE | 0.913 | 1M $(C_2H_5)_4NBF_4$ | 0.0-2.5 | 3,000 | 80 |
| nM7M-MOF-74 | 1.155 | 1M $(C_2H_5)_4NBF_4$ | 0.0-2.5 | 300 | 80 |
| nHKUST-1 | 2.33 | 1M $(C_2H_5)_4NBF_4$ | 0.0-2.5 | 6,000 | 80 |
| nMOF-177 | 0.713 | 1M $(C_2H_5)_4NBF_4$ | 0.0-2.5 | 4,000 | 80 |
| nZIF-8 | 0.268 | 1M $(C_2H_5)_4NBF_4$ | 0.0-2.5 | 2,500 | 80 |
| nUIO-66 | 1.945 | 1M $(C_2H_5)_4NBF_4$ | 0.0-2.5 | 7,000 | 80 |
| nMOF-867 | 5.085 | 1M $(C_2H_5)_4NBF_4$ | 0.0-2.5 | 10,000 | 80 |
| activated carbon | 0.788 | 1M $(C_2H_5)_4NBF_4$ | 0.0-2.5 | 10,000 | 80 |
| graphene | 0.515 | 1M $(C_2H_5)_4NBF_4$ | 0.0-2.5 | 10,000 | 80 |

Figure 23A:
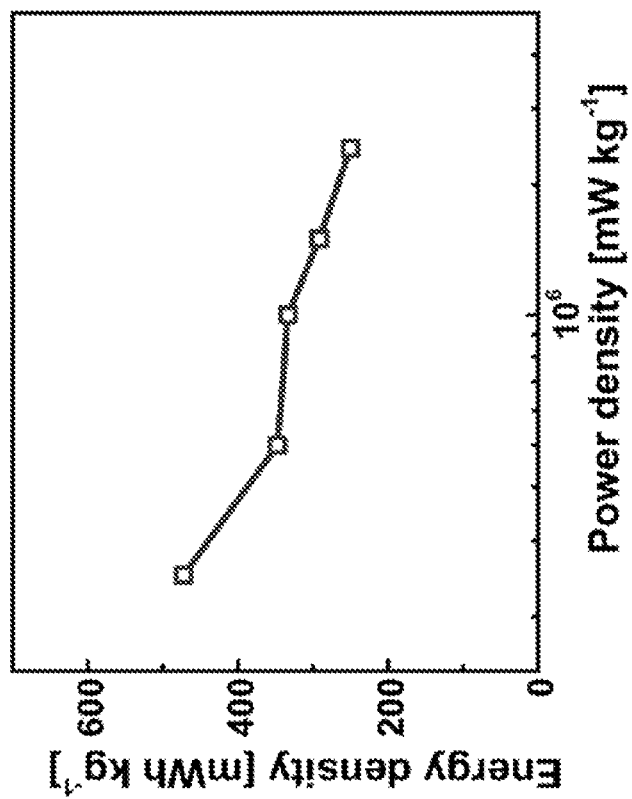
FIGS. 23A-23B are graphical views of (a) Cell capacitance of the Zr-BTD-NDI-BPy-MOF symmetric devices and (b) Ragone plots showing the energy density of power density, according to one or more embodiments of the present disclosure.
Figure 23B:
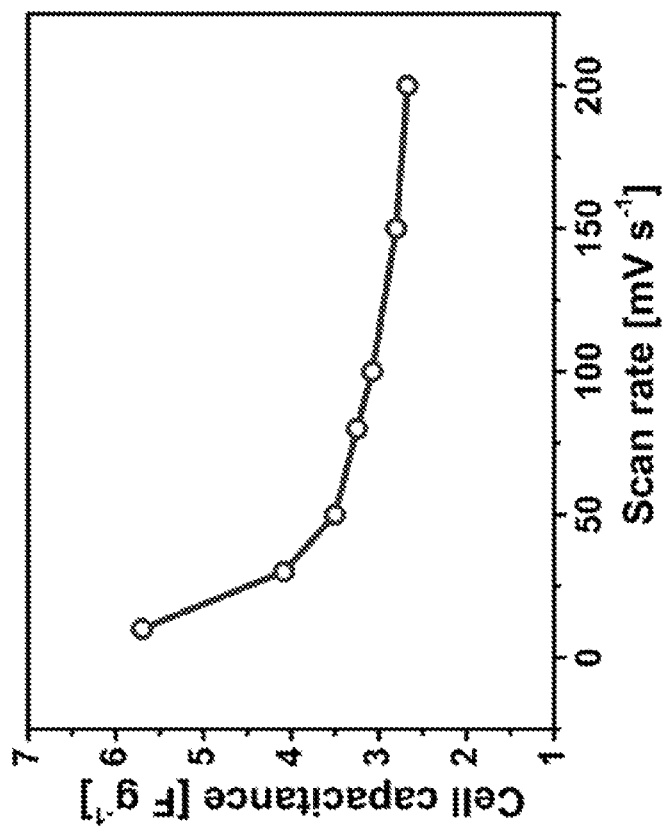

The energy density and the power density were further examined for the Zr-BTD-NDI-BPy-MOF and the result was presented as the Ragone plot in FIG. 23b. The device delivered an energy density of 472 mWh kg$^{-1}$ at a power density of 250 Wh kg$^{-1}$.

In conclusion, a Zr-BTD-NDI-MOF having an organic linker with a redox active core was successfully and for the first time designed and synthesized. A MOF possessing high surface area and redox core that can provide both electric double layer and pseudo capacitances, and be used as a supercapacitor electrode, was deliberately developed. The incorporation of the redox process as demonstrated was responsible for the pseudo-capacitance (i.e. store electrical energy via chemical energy) in the MOF. The Zr-BTD-NDI-MOFs was then post-synthetically modified to Zr-BTD-NDI-BP-MOF and Zr-BTD-NDI-BPy-MOF, which increased rigidity to the pristine structure and led to the enhancement in the surface area and as a result increased their capacitance performance. In addition, the Zr-BTD-NDI-BPy-MOFs exhibited uniform porosity distribution, which aided rapid ion transport without blocking the accessible surface area.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. An electrode material, comprising:
   a hexanuclear metal ion cluster; and
   an organic linker with a redox-active center, wherein the organic linker with the redox-active center is N,N'-bis(terphenyl-4,4"-dicarboxylic acid) naphthalenediimide (BTD-NDI), wherein NDI is the redox-active center,
   wherein the organic linker associates with the metal ion cluster to form a metal-organic framework.

2. The electrode material of claim 1, wherein the electrode material is post-functionalized with an organic pillar selected from 4,4'-biphenyl-dicarboxylic acid, 2,2-bipyridine-4,4-dicarboxylic acid and 3,3-dihydroxybiphenyl-4,4-dicarboxylic acid.

3. The electrode material of claim 2, wherein the organic pillar is biphenyl-dicarboxylic acid (BPD).

4. The electrode material of claim 1, wherein the metal ion clusters are characterized by the formula $[M_6O_4(OH)_4]^{8+}$, where M is selected from alkali metals and combinations thereof, rare-earth metals, transition metals, lanthanides, and/or post-transition metals.

5. The electrode material of claim 4, wherein M is one or more of Zr, Hf, La, Ce, Pr, Nd, Sm, Eu, Gd, Dy, Ho, Er, Tm, Yb, Lu, Tb, and Y.

6. The electrode material of claim 1, wherein the metal-organic framework has scu topology.

7. The electrode material of claim 1, wherein the metal-organic framework is Zr-NDI-MOF and/or Zr-NDI-BPD-MOF.

8. A method of forming an electrode material, comprising:
   contacting a metal ion cluster with an organic linker including a redox-active center to form a metal-organic framework, wherein the organic linker including the redox-active center is N,N'-bis(terphenyl-4,4"-dicarboxylic acid) naphthalenediimide (BTD-NDI), wherein NDI is the redox-active center.

9. The method of claim 8, further comprising modifying the metal-organic framework via post-functionalization with an organic pillar selected from 4,4'-biphenyl-dicarboxylic acid, 2,2-bipyridine-4,4-dicarboxylic acid and 3,3-dihydroxybiphenyl-4,4-dicarboxylic acid.

10. The method of claim 9, wherein the organic pillar is biphenyl-dicarboxylic acid.

11. The method of claim 8, wherein the metal ion clusters are characterized by the formula $[M_6O_4(OH)_4]^{8+}$, where M is selected from alkali metals and combinations thereof, rare-earth metals, transition metals, lanthanides, and/or post-transition metals.

12. The method of claim 8, wherein M is one or more of Zr, Hf, La, Ce, Pr, Nd, Sm, Eu, Gd, Dy, Ho, Er, Tm, Yb, Lu, Tb, and Y.

13. The method of claim 8, wherein the metal-organic framework has scu topology.

* * * * *